(12) United States Patent
Saini

(10) Patent No.: US 12,318,331 B2
(45) Date of Patent: Jun. 3, 2025

(54) INTRAOCULAR LENS DOCKING STATION

(71) Applicant: Manjinder Saini, Germantown, TN (US)

(72) Inventor: Manjinder Saini, Germantown, TN (US)

( * ) Notice: Subject to any disclaimer, the term of this patent is extended or adjusted under 35 U.S.C. 154(b) by 0 days.

(21) Appl. No.: 18/749,962

(22) Filed: Jun. 21, 2024

(65) Prior Publication Data
US 2024/0423840 A1  Dec. 26, 2024

Related U.S. Application Data

(60) Provisional application No. 63/522,623, filed on Jun. 22, 2023.

(51) Int. Cl.
*A61F 9/08* (2006.01)
*A61F 2/16* (2006.01)
*A61F 2/48* (2006.01)

(52) U.S. Cl.
CPC .............. *A61F 9/08* (2013.01); *A61F 2/1648* (2013.01); *A61F 2/482* (2021.08); *A61F 2002/1682* (2015.04); *A61F 2250/0002* (2013.01); *A61F 2250/0059* (2013.01); *A61F 2250/0063* (2013.01)

(58) Field of Classification Search
CPC .................................. A61F 9/08; A61F 2/1648
See application file for complete search history.

(56) References Cited

U.S. PATENT DOCUMENTS

| | | | |
|---|---|---|---|
| 5,800,530 A * | 9/1998 | Rizzo, III | G02B 3/14 623/6.22 |
| 9,662,199 B2 * | 5/2017 | Grant | A61F 2/1624 |
| 2002/0128710 A1 | 9/2002 | Eggleston | |
| 2005/0119740 A1 * | 6/2005 | Esch | A61F 2/1635 623/6.37 |
| 2016/0113760 A1 * | 4/2016 | Conrad | A61F 2/1648 623/6.22 |
| 2018/0353332 A1 * | 12/2018 | Saini | A61F 2/1624 |
| 2019/0069989 A1 * | 3/2019 | Otts | G02C 7/085 |
| 2020/0197157 A1 | 6/2020 | Shmukler et al. | |
| 2021/0290441 A1 * | 9/2021 | Wiemer | A61B 5/076 |
| 2021/0382326 A1 * | 12/2021 | Kubota | G02C 7/022 |
| 2022/0313422 A1 | 10/2022 | Buchheister et al. | |
| 2023/0149220 A1 | 5/2023 | Saini | |

OTHER PUBLICATIONS

International Search Report and Written Opinion issued in related Application Serial No. PCT/US2024/035071 on Oct. 14, 2024.

* cited by examiner

*Primary Examiner* — Melanie R Tyson
*Assistant Examiner* — Yasniary De La Caridad Morales
(74) *Attorney, Agent, or Firm* — Holland & Knight, LLP; Matthew C. Cox

(57) ABSTRACT

An intraocular implant device is provided. The implant device may include a dock and a removable lens device (RLD) shaped for positioning inside the lens chamber of the eye. The dock may include a first frame, a power supply, and a controller. The RLD may include a second frame, a projector, and an electromechanical lens array. The second frame may be configured to replaceably attach to the first frame, such that RLD is replaceably attached to the dock.

30 Claims, 17 Drawing Sheets

INTRAOCULAR LENS DOCKING STATION

CROSS-REFERENCES TO RELATED APPLICATION

This application is a non-provisional of and claims priority to and benefit of U.S. Provisional Patent Application No. 63/522,623, filed Jun. 22, 2023, entitled INTRAOCULAR LENS DOCKING STATION, which is hereby incorporated by reference in its entirety.

STATEMENT REGARDING FEDERALLY SPONSORED RESEARCH OR DEVELOPMENT

Not Applicable.

REFERENCE TO SEQUENCE LISTING OR COMPUTER PROGRAM LISTING APPENDIX

Not Applicable.

BACKGROUND

The present disclosure relates generally to ophthalmologic devices for implantation into the eye, and more particularly to intraocular implant devices and associated power supplies for enhancing or restoring vision in humans and animals.

Over the last few decades, vision related problems in rate of occurrence, age of onset, and severity are becoming increasingly worse to the point it is becoming alarming in the vision care industry. One cause appears to be humans increasingly spending more time viewing electronic display screens. Over time, although display technology improved, people began spending more time looking at electronic displays, including home computers, televisions and mobile electronic devices, often in harsh environments such as full sunlight. As people continue to spend more and more time viewing electronic displays such as small screens in harsh conditions such as sunlight, vision problems continue to increase.

Many people experience impaired vision as a result of corneal dysfunction or damage, lens dysfunction or damage, or other conditions of the eye that lead to inability of light to properly pass through the lens chamber of the eye to the retina. Various medical procedures have been developed to attempt to correct these types of problems to improve or to restore vision. For example, lens replacement procedures are often used to remove a damaged or occluded lens from the lens chamber of the eye. In some cases, an artificial intraocular implant device may be inserted to replace the lens. Many conventional procedures are currently known for removal of a damaged or occluded lens from the lens chamber. For example, in cataract surgery a damaged lens may be phacoemulsified using a tool to break up the lens. The broken-up lens may then be aspirated from the eye using a negative pressure, and replaced with a liquid solution to maintain the form of the empty lens chamber. Following such procedures, an implant device such as an intraocular lens may be inserted into the empty lens chamber using known tools and techniques. While the field of intraocular lens devices may have proliferated into powered and intelligent devices, significant improvement in the field is required. For instance, there exists a need for intraocular lens devices with enhanced design flexibility, upgradeability, replace-ability, and the like.

As a particular example, in some cases of an implant device inserted into the eye to replace a damaged or occluded lens, the implant device may degrade over time (e.g., fail to properly pass light to the retina). Typically, such degraded implant devices must be replaced through surgical procedures as described above (e.g., removing the degraded device, inserting a new device). Each such surgical procedure is typically invasive and may damage tissue in the eye, particularly the lens chamber therein. For instance, it has been suggested that only three such surgical procedures should be conducted to avoid substantial tissue damage to the eye. Moreover, even a single such procedure may require extensive healing times and may cause other complications in the eye. It would be advantageous to provide an intraocular implant device that may be repaired or partially replaced without such surgical procedures.

What is needed are improvements in devices and methods for improving or restoring vision in patients with impaired cornea or lens tissue in the eye.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

One aspect of the present disclosure is an intraocular implant device. The intraocular implant device may include an intraocular lens docking station (dock) shaped for positioning inside a lens chamber of an eye. The dock may include a dock body having an anterior side facing a cornea of the eye and a posterior side facing a retina of the eye, a first frame disposed on the dock body, a power supply disposed on the dock body within the first frame, and a controller disposed on the dock body within the first frame. The device may further include a removable lens device (RLD) shaped for positioning inside the lens chamber of the eye and configured for replace-able attachment with the dock. The RLD may include an RLD body having an anterior side facing the cornea of the eye and a posterior side facing the retina of the eye, and a second frame disposed on the RLD body. The second frame of the RLD may be configured to replaceably attach to the first frame of the dock, such that the posterior side of the RLD body is replaceably attached to the anterior side of the dock body. In such embodiments, the replaceable feature allows the second frame to removably or interchangeably interconnect with the first frame such that the second frame may be mechanically connected to the first frame, and may be later detached and removed and/or re-installed without damaging either frame.

In some embodiments, the RLD further includes an electromechanical lens array disposed on the RLD body within the second frame. The electromechanical lens array may include one or more lenses configured to receive incident light through the cornea, convert the incident light into a focused image, and transmit the focused image to the retina. The electromechanical lens array may be configured to receive electrical power from the power supply of the dock when the RLD is attached to the dock and one or more control signals from the controller when the RLD is attached to the dock, such that the electromechanical lens array is operable to adjust an axial position of the one or more lenses based on the one or more control signals to increase a clarity of the focused image.

In some embodiments, the RLD further includes a projector disposed on the RLD body within the second frame. The projector may be configured to receive electrical power from the power supply of the dock when the RLD is attached to the dock and one or more control signals from the controller when the RLD is attached to the dock, such that the projector is operable to emit photons onto the retina in a pattern representative of focused image data based on the one or more control signals.

Another aspect of the present disclosure is a method of improving vision in a patient. The method may include providing an intraocular lens docking station (dock) within a lens chamber of an eye. The dock may include a dock body having an anterior side facing a cornea of the eye and a posterior side facing a retina of the eye, a first frame disposed on the dock body, a power supply disposed on the dock body within the first frame, and a controller disposed on the dock body within the first frame. The method may further include providing a removable lens device (RLD). The RLD may include an RLD body having an anterior side facing the cornea of the eye and a posterior side facing the retina of the eye, a second frame disposed on the RLD body, and an electromechanical lens array disposed on the RLD body within the second frame, the electromechanical lens array including one or more lenses.

The method may further include securing the RLD to the dock within the lens chamber of the eye. The RLD may be secured to the dock via the second frame mechanically engaging the first frame, such that the posterior side of the RLD body is replaceably attached (e.g., replaceably engaged, replaceably attached, removably engaged, etc.) with the anterior side of the dock body. The method may further include receiving, via one or more lenses, incident light through the cornea; converting, via the one or more lenses, the incident light into a focused image; transmitting, via the one or more lenses, the focused image to the retina; and receiving, via the electromechanical lens array, electrical power from the power supply of the dock. The method may further include transmitting, via the controller, one or more control signals to the electromechanical lens array, such that the electromechanical lens array is operable to adjust an axial position of the one or more lenses based on the one or more control signals to increase a clarity of the focused image.

Numerous other objects, advantages and features of the present disclosure will be readily apparent to those of skill in the art upon a review of the following drawings and description of a preferred embodiment.

DETAILED DESCRIPTION

Figure 1:
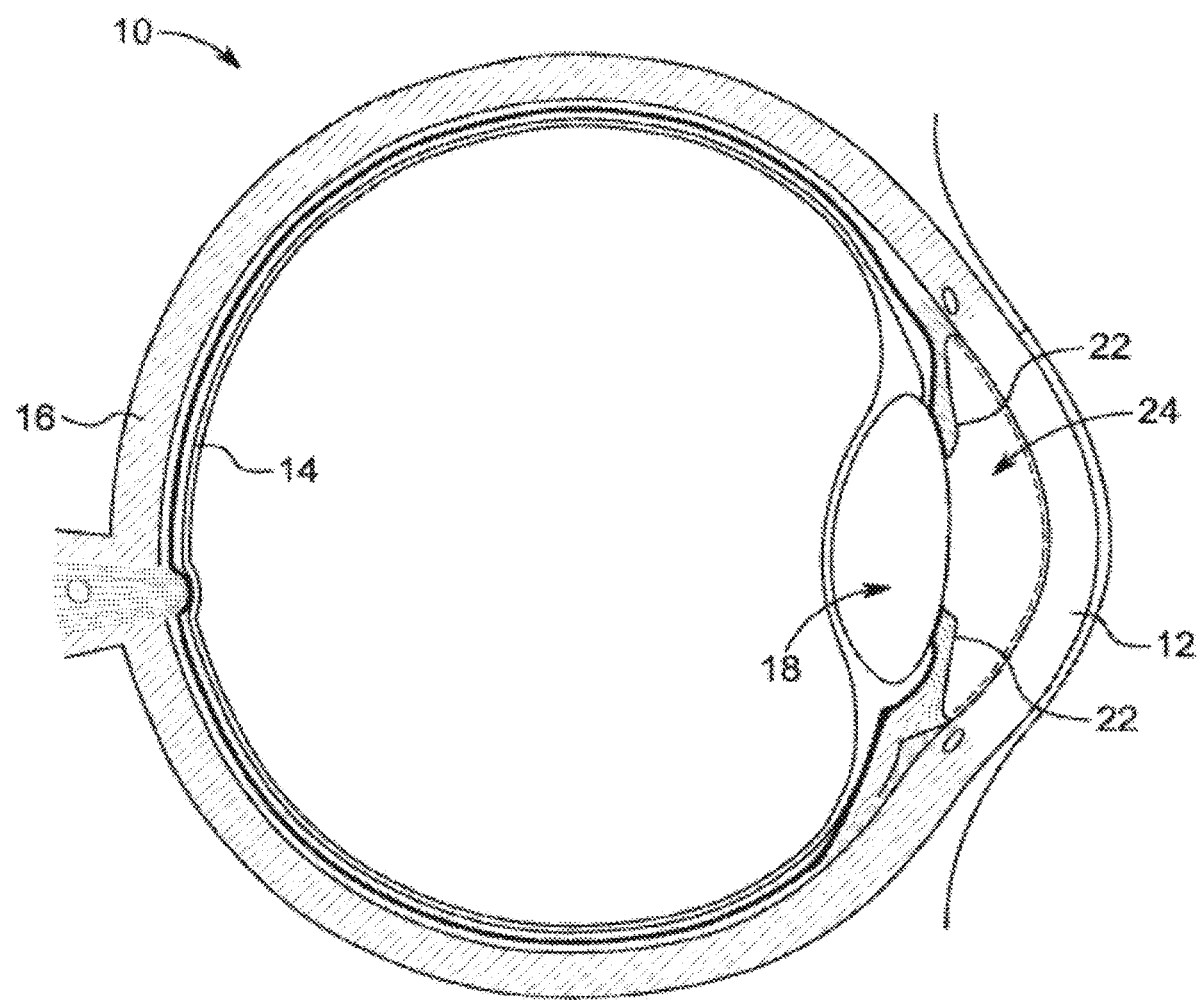
FIG. 1 is a schematic view of an embodiment of an eye with an open lens chamber having a natural lens removed.

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention. Those of ordinary skill in the art will recognize numerous equivalents to the specific apparatus and methods described herein. Such equivalents are considered to be within the scope of this invention and are covered by the claims.

In the drawings, not all reference numbers are included in each drawing, for the sake of clarity. In addition, positional terms such as "upper," "lower," "side," "top," "bottom," etc. refer to the apparatus when in the orientation shown in the drawing, or as otherwise described. A person of skill in the art will recognize that the apparatus can assume different orientations when in use.

Referring now to FIG. 1, an example schematic of an eye 10 is shown, according to some embodiments of the present disclosure. The eye 10 may include a cornea 12, a retina 14, a sclera 16, a lens chamber 18, an iris 22, and an anterior chamber 24. For example, incoming light (e.g., incident light 56 depicted with reference to FIGS. 3-8) entering the eye 10 may travel through the cornea 12 and into the anterior chamber 24, into a lens typically positioned within the lens chamber 18 via an opening formed by the iris 22, be adjusted (e.g., refracted, focused, etc.) in the lens chamber 18, and be received by the retina 14 as an image 58 (depicted with reference to FIGS. 3-8) on the opposite side of the eye 10. As mentioned above, various conditions of the eye 10 (such as a damaged or occluded lens in the lens chamber 18) that lead to the inability of light to pass through components of the eye 10 to the retina 14 may be treated with lens replacement and, in some cases, insertion of an intraocular implant device.

Figure 2:
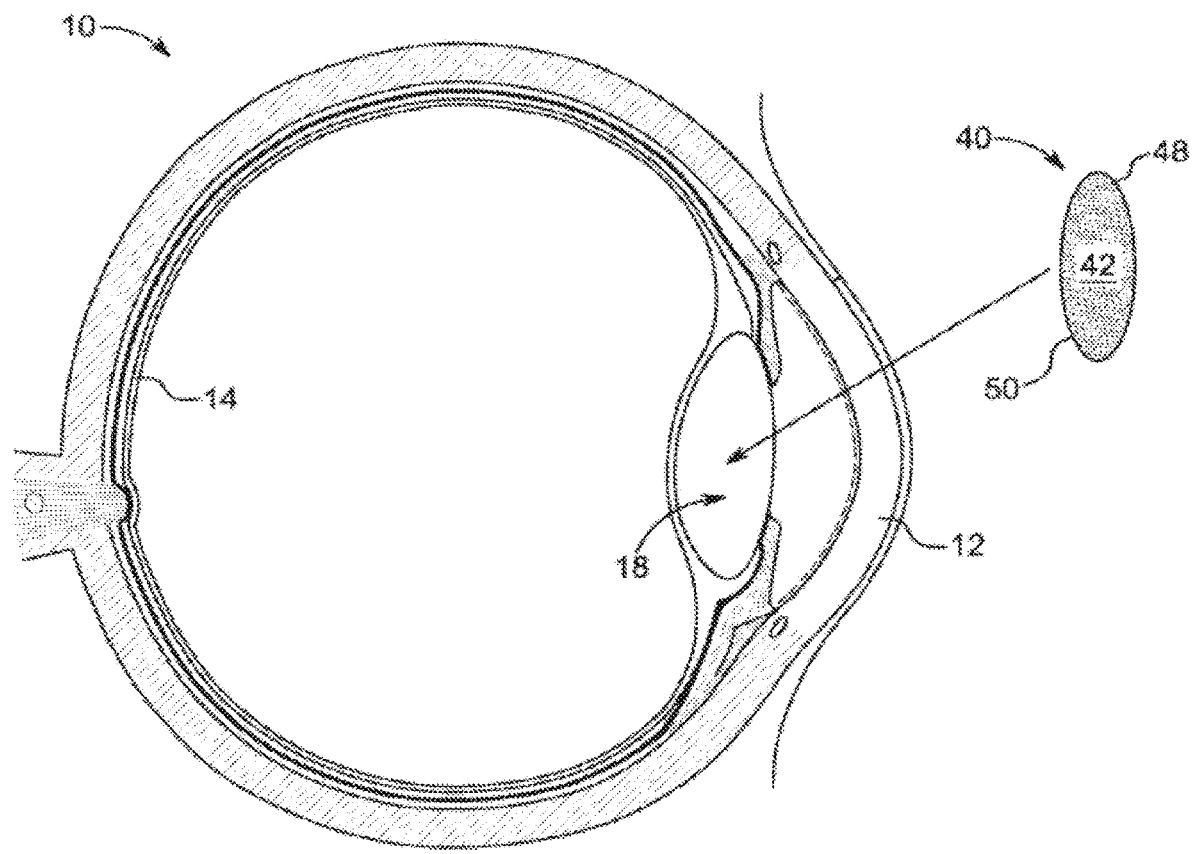
FIG. 2 is a schematic view of an embodiment of an eye with an intraocular implant device in accordance with the present disclosure positioned for implantation into the open lens chamber of the eye.

Referring now to FIG. 2, an introductory embodiment of an improved intraocular implant device (device) 40 for implantation into the lens chamber 18 is shown, according to some embodiments of the present disclosure. The device 40 is depicted outside of the eye 10 for implantation into the empty lens chamber 18 of the eye 10. In general, the device 40 is an intraocular implant device that includes a main body 42 having an anterior side 48 positioned to face the cornea 12 after implantation, and a posterior side 50 positioned to face the retina 14 after implantation. The device 40 includes numerous technological innovations, and is operable to provide artificial sight improvement or sight restoration. In particular, the device 40 may include two distinct components: an intraocular lens docking station (dock) 140 (depicted with reference to FIGS. 3-5), and a removable lens device (RLD) 240 (depicted with reference to FIGS. 6-8). The dock 140 may be implanted into the lens chamber 18 of the eye 10 as discussed above. Advantageously, however, the dock 140 may include various components that are not subject to degradation that requires the invasive replacement discussed above. Rather, such components (such as an improved lens) may be located on the RLD 240, which may be replaced with less invasive surgery from time-to-time via a removable attachment (e.g., mechanical engagement) between the dock 140 and the RLD 240. Accordingly, while generally referred to herein as a "dock," the dock 140 may otherwise be understood as a support structure, a holder, a cradle, and so on, insofar as the dock 140 is structured to receive and retain the RLD 240 within the lens chamber 18.

In some embodiments, the dock 140 defines a dock body 142, and the RLD 240 defines an RLD body 242. The dock and RLD bodies 142, 242 in turn, may make up the main body 42 of the device 40. In some embodiments, the dock and/or RLD bodies 142, 242 are flexible or foldable. In other embodiments, the dock and/or RLD bodies 142, 242 are segmented (e.g., comprised of two lateral halves, two vertical halves, three portions, four portions, etc.). In other embodiments still, the dock and/or RLD bodies 142, 242 are collapsible. Advantageously, such flexibility, foldability, segmentation, and/or collapsibility may provide for a smaller incision and ease of implantation of the device 40.

As discussed above, the device 40 (e.g., both the dock and RLD bodies 142, 242) may be inserted into the empty lens chamber 18 for intraocular improvements as discussed herein. However, in some implementations of the present disclosure, only the dock body 142 is initially inserted into the empty lens chamber 18, and the RLD body 242 is later inserted (e.g., replaceably attached to the dock body 142). As described in greater detail below, the dock 140 and/or the RLD 240 may include various photoelectric arrays for generating power for components of the device 40. As a first example, the dock 140 may include a first photoelectric array 144. As a second example, the RLD 240 may include a second photoelectric array 244. As a third example, the dock 140 may further include a third photoelectric array 174.

Figure 3:
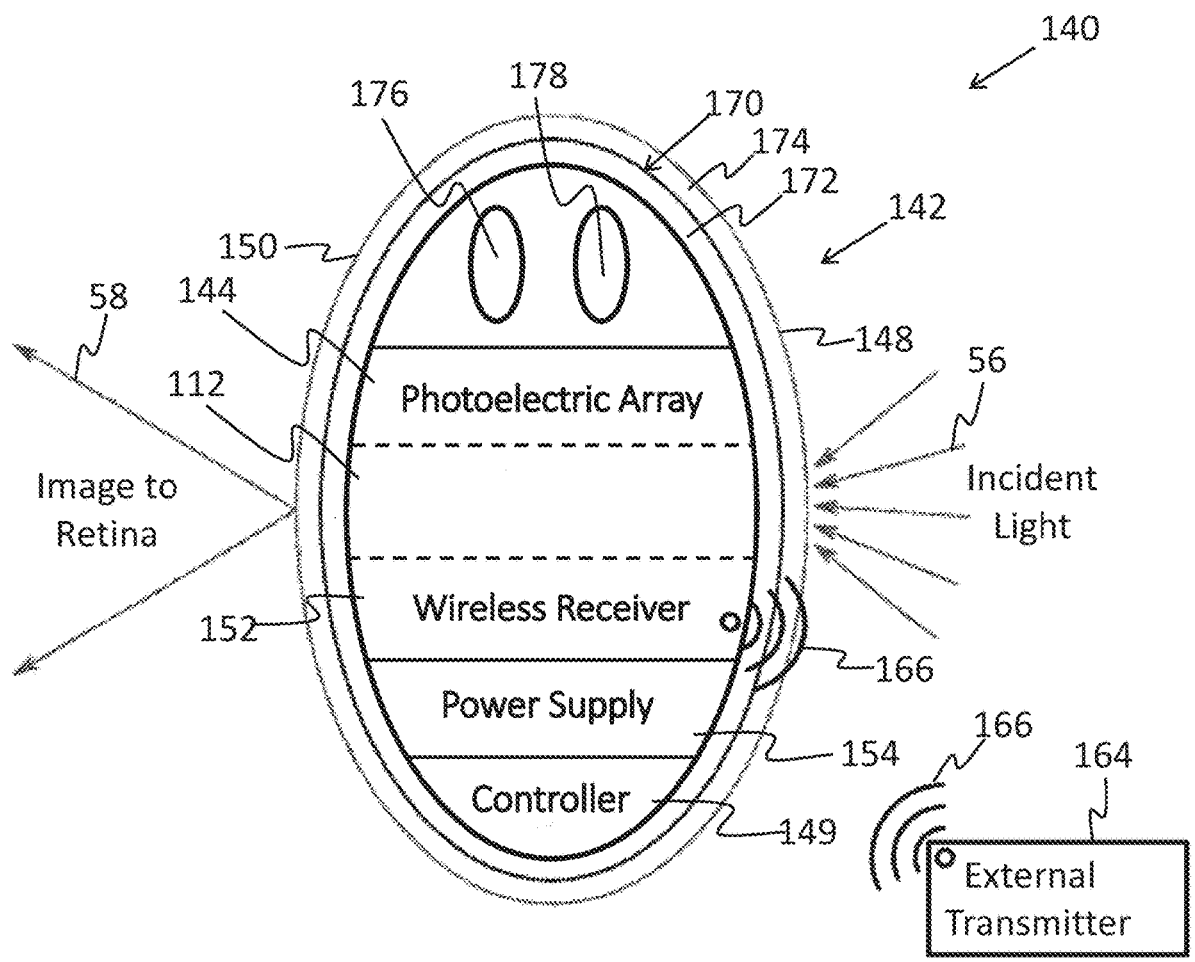
FIG. 3 is a schematic view of an intraocular lens docking station (dock) of an intraocular implant device in accordance with the present disclosure.

Referring now to FIG. 3, the dock 140 of the device 40 is shown, according to some embodiments of the present disclosure. As mentioned above, the dock 140 may include the dock body 142. The dock body 142 may define an anterior side 148 and a posterior side 150 (corresponding to the anterior side 48 and the posterior side 50 of the main body 42 of the device 40). As discussed in greater detail below, the dock 140 may include various components disposed on the dock body 142 such as the first photoelectric array 144, a controller 149, a receiver or transceiver (e.g., a wireless receiver, receiver/transmitter, wireless communication device, etc.) 152, a power supply 154, a first power bus 176, an orifice 112, and/or a second power bus 178. One or more of the aforementioned components may be disposed on the dock body 142 as bounded by a frame (e.g., hoop) 170 that may include various components such as first mechanical interface 172 and/or the third photoelectric array 174. The various aforementioned components may be positioned at any suitable location on the dock 140 and define a common circuit board structure with one another, as described in greater detail below with reference to FIG. 4. As discussed in greater detail below, when the RLD 240 is attached to the dock 140, the common circuit board structure formed by the components of the dock 140 may be joined with a common circuit board structure formed by one or more components of the RLD 240.

As discussed herein, the dock 140 may include various components disposed on the dock body 142. In some embodiments, such components are permanently affixed to the dock body 142. In other embodiments, such components are replaceably attached to the dock body 142, such that the components may be replaced. For instance, such components may be attached to the dock body 142 via pin-and-socket configurations, or any other suitable electrical or mechanical interface. Advantageously, replacement of the components of the dock 140 may allow for less frequent replacement of the RLD 240 itself. Moreover, the present disclosure may allow for minimizing the size of the device 40 itself, as well as lowering the earliest viable age of implantation for such devices on users.

As suggested above, the dock body 142 of the dock 140 may be bound by the first frame 170. In some embodiments, the first frame 170 defines a substantially ovular shape. In other embodiments, the first frame 170 defines a substantially circular shape. In other embodiments still, the first frame 170 defines a substantially elliptical shape. Of course, one of skill in the art will appreciate that the frame 170 (and, therefore, the entire dock 140 and the device 40 thereon) may be formed in any suitable shape for insertion within the lens chamber 18 of the eye 10. As mentioned above, the first frame 170 may include the first mechanical interface 172. The first mechanical interface 172 may be operable to mechanically engage a corresponding second mechanical interface 272 of the RLD 240 (depicted with reference to FIG. 7) when the RLD 240 is replaceably attached to the dock 140, thereby securing the RLD 240 to the dock 140. The mechanical engagement between the first and second mechanical interfaces 172, 272 is discussed in greater detail below with reference to FIG. 8.

In some embodiments, each of the first and third photoelectric arrays 144, 174 may each include one or more photoelectric sensors positioned on the anterior side 148. Such photoelectric sensors may include any suitable photovoltaic or photoelectric sensors known in the art capable of converting incident light (e.g., an incoming light beam) 56 received upon the first and/or third photoelectric arrays 144, 174 into electrical power. The first and third photoelectric arrays 144, 174 may each include at least one electrical output operable to transmit electrical power to a circuit component, as discussed in greater detail below with reference to FIG. 4. In some embodiments, the first and third photoelectric arrays 144, 174 may be activated (to initiate conversion of the incident light 56 to electrical power and transmit the electrical power to other components) and, conversely, deactivated. Such activation and deactivation may be controlled by the controller 149 as described in greater detail below with reference to FIG. 12. In some embodiments, the photoelectric sensor includes a plurality of stacked photoelectric p-n junctions, wherein each stacked photoelectric p-n junction is receptive to a specific bandwidth of light frequencies. In further embodiments, the photoelectric sensor includes a picture element operable to detect chrominance and luminance of the light received by the photoelectric sensor.

Depending on the implementation of the present disclosure, the first and third photoelectric arrays 144, 174 may each cover distinct portions of the surface of the anterior side 148 of the dock body 142 of the dock 140. In particular, the first photoelectric array 144 may cover a portion of the anterior side 148 within the first frame 170, while the third photoelectric array 174 may cover a portion of the anterior side on the first frame 170. In particular, the third photoelectric array 174 may be arranged in a loop bounding the outer perimeter of the first mechanical interface 172 of the first frame 170. Advantageously, by locating the first and third photoelectric arrays 144, 174 on distinct portions of the dock body 142, the first and third photoelectric arrays 144, 174 may be selectively operated (e.g., activated or deactivated as mentioned above), based on whether the RLD 240 is attached to the dock 140, as described in greater detail below with reference to FIG. 12.

In some embodiments, the power supply 154 includes any suitable power converter or power storage device for operation of the dock 140 (and, as discussed below with reference to FIG. 9, the device 40 in its entirety). The power supply 154 may include a battery configured for storing electrical power generated by one or more components of the dock 140 for later use by one or more other circuit components, as described in greater detail below with reference to FIG. 4.

In some embodiments, the controller 149 may be any suitable controller positioned on the dock 140 to be in communication with and/or control one or more of the various components of the dock 140 such as the power supply 154, the receiver or transceiver 152, the first photoelectric array 144, the first power bus 176, and the first data bus 178. The function of the controller 149 is described in greater detail below with reference to FIG. 4. Further, when the RLD 240 is attached to the dock 140, the controller 149 may be in communication with and/or control one or more components of the RLD 240, as discussed in greater detail below with reference to FIG. 9.

In some embodiments, the receiver 152 is configured to receive an input signal 166 from an external transmitter 164. As depicted with reference to FIG. 4, the receiver 152 may provide the input signal 166 to the controller 149. Accordingly, in some embodiments, the receiver 152 and the controller 149 are provided as a single component. As discussed in greater detail below with reference to FIG. 9, the input signal 166 may include information associated with control (via the controller 149) of one or more components of the RLD 240 when the RLD 240 is attached to the dock 140. The external transmitter 164 may include any suitable external device for communicating the input signal 166 to the receiver 152. Any suitable wireless signal transmission protocol for transmitting data or analog signals may be used for the input signal 166. In some embodiments, one or more antennae are connected to the receiver 152 in order to enhance reception of the input signal 166 from the external transmitter 164.

Figure 4:
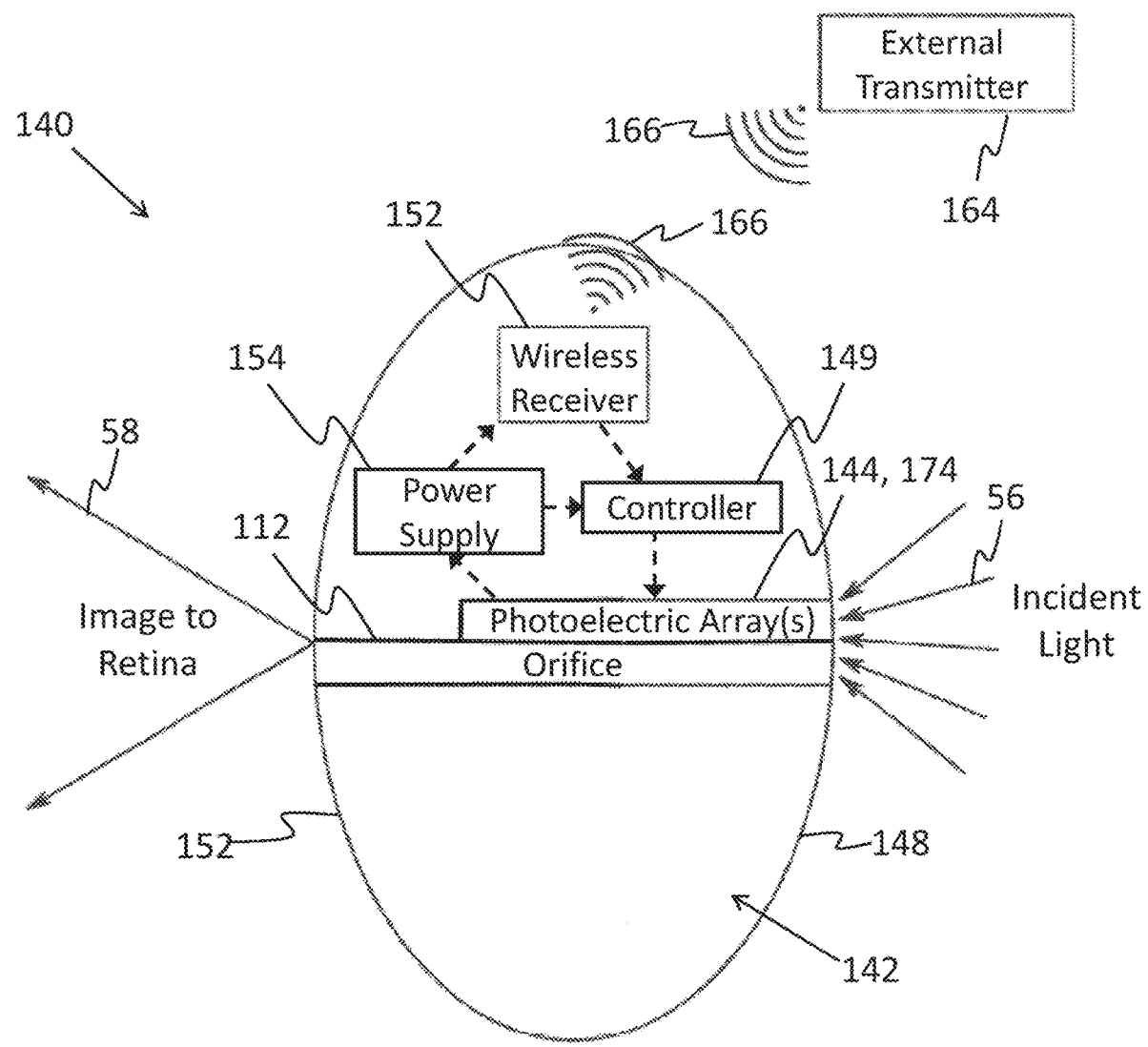
FIG. 4 is a schematic view of a dock of an intraocular implant device in accordance with the present disclosure.

In some embodiments, the orifice 112 is an open portion of the dock body 142 that allows the incident light 56 to pass through the dock body 142 and to the retina 14, as further depicted with reference to FIG. 4. Accordingly, when the RLD 240 is not attached to the dock 140, the incident light 56 may pass through the dock 140 and the eye 10 may function as an eye without internal lens (aphakic configuration).

Referring now to FIG. 4, operation of the dock 140 is shown, according to some embodiments of the present disclosure. As mentioned above with reference to FIG. 3, the power supply 154 may store electrical power generated by one or more components of the dock 140 for later use by one or more other circuit components. In some embodiments, the power supply 154 is configured to store electrical power generated by the first and/or third photoelectric arrays 144, 174. For example, as mentioned above, the first and third photoelectric arrays 144, 174 may be operable to transmit electrical power to a circuit component. In this sense, the first and/or third photoelectric arrays 144, 174 may be coupled to the power supply 154 and transmit the electrical power to the power supply 154, thereby "recharging" the power supply 154. Further, and as described in greater detail below with reference to FIG. 9, the power supply 154 may be recharged by one or more components of the RLD 240 when the RLD 240 is attached to the dock 140.

As generally discussed herein, the dock 140 includes the first and third photoelectric arrays 144, 174. In other embodiments of the present disclosure, the dock 140 may only include the first photoelectric array 144 or only the third photoelectric array 174. In other embodiments still, neither of the first and third photoelectric arrays 144, 174 are included in the dock 140. For example, the power supply 154 may be solely recharged by one or more components of the RLD 240 when the RLD 240 is attached to the dock 140.

Depending on the implementation, the power supply 154 may be continuously recharging as additional incident light 56 is received by the first, second, and/or third photoelectric arrays 144, 244, 174. In turn, the power supply 154 may be simultaneously distributing electrical power to other circuit components. For example, the power supply 154 may be configured to distribute electrical power to various components of the dock 140 such as the receiver 152 and the controller 149. In further embodiments where the first mechanical interface 172 (depicted with reference to FIG. 3) uses electromechanical components to engage the second mechanical interface 272 of the RLD 240 when the RLD 240 engages the dock 140, the power supply 154 may be further configured to distribute power to the first mechanical interface 172 and/or the second mechanical interface 272.

In some embodiments, and as described in greater detail below with reference to FIG. 9, the power supply 154 may be further configured to distribute electrical power to various components of the RLD 240 via the first power bus 176 of the dock 140 (depicted with reference to FIG. 3) when the RLD 240 is replaceably attached to the dock 140. In general, the first power bus 176 and/or the first data bus 178 (depicted with reference to FIG. 3) may be configured to exchange power and/or data with various components of the RLD 240 when the RLD 240 is replaceably attached to the dock 140.

As mentioned above, the controller 149 may be in communication with and/or control one or more of the various components of the dock 140. As a first example, and as mentioned above with reference to FIG. 3, the receiver 152 may provide the input signal 166 to the controller 149. As a second example, and as discussed in greater detail below with reference to FIG. 12, the controller 149 may be configured to selectively activate and/or deactivate the first and/or third photoelectric arrays 144, 174 based on whether the RLD 240 is replaceably attached to the dock 140. As a third example, and as discussed in greater detail below, the controller 149 may analyze the amount of light received by the device 40 (when the dock 140 is engaged with the RLD 240) and control components of the device 40 accordingly.

Figure 5:
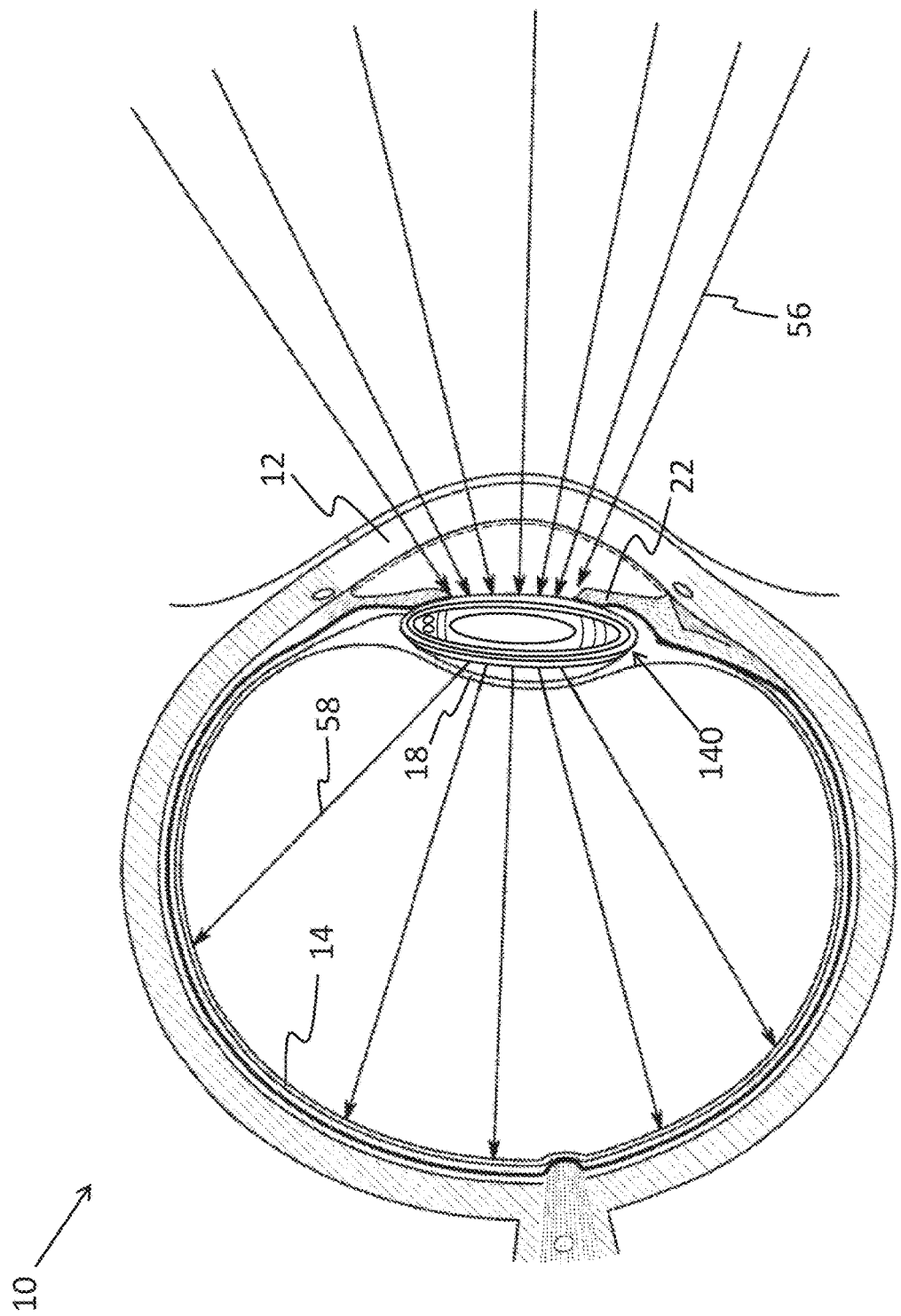
FIG. 5 is a schematic view of an embodiment of dock of an intraocular implant device within the lens chamber of an eye in accordance with the present disclosure.
Figure 6:
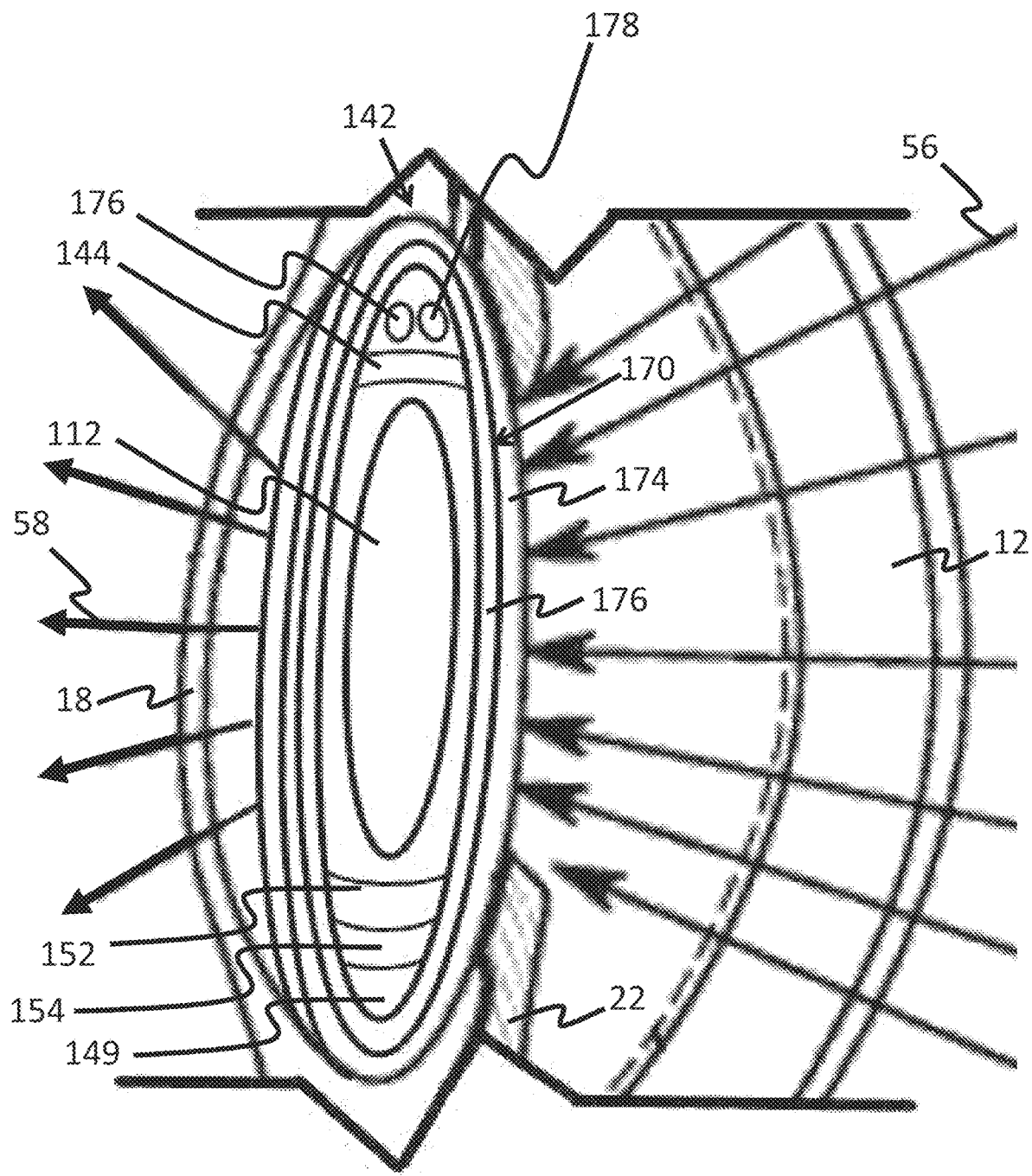
FIG. 6 is a detailed schematic view of an embodiment of dock of an intraocular implant device within the lens chamber of an eye in accordance with the present disclosure.

Referring now to FIGS. 5-6, the dock 140 is shown inserted into the lens chamber 18 of the eye 10, according to some embodiments of the present disclosure. For example, the dock 140 may be implanted into the empty lens chamber 18 using known tools and techniques as discussed above. As mentioned above, in cases of a conventional intraocular implant device being inserted into the eye to replace a damaged or occluded lens, the device may degrade over time, typically requiring additional invasive surgical procedures. Advantageously, however, the aforementioned components of the dock 140 may not be subject to the typical degradation that otherwise necessitates potential replacement. Such components may be located on the RLD 240 which, as described herein, may be easily replaceable with less invasive surgery, while the dock 140 remains permanently (or relatively so) within the lens chamber 18 of the eye 10. Alternatively, in some embodiments, one or more of the various components on the RLD are rigidly or permanently affixed to the RLD and are not modular or removable. In further embodiments, one or more of the various components on the RLD are modular and are replaceable.

Figure 7:
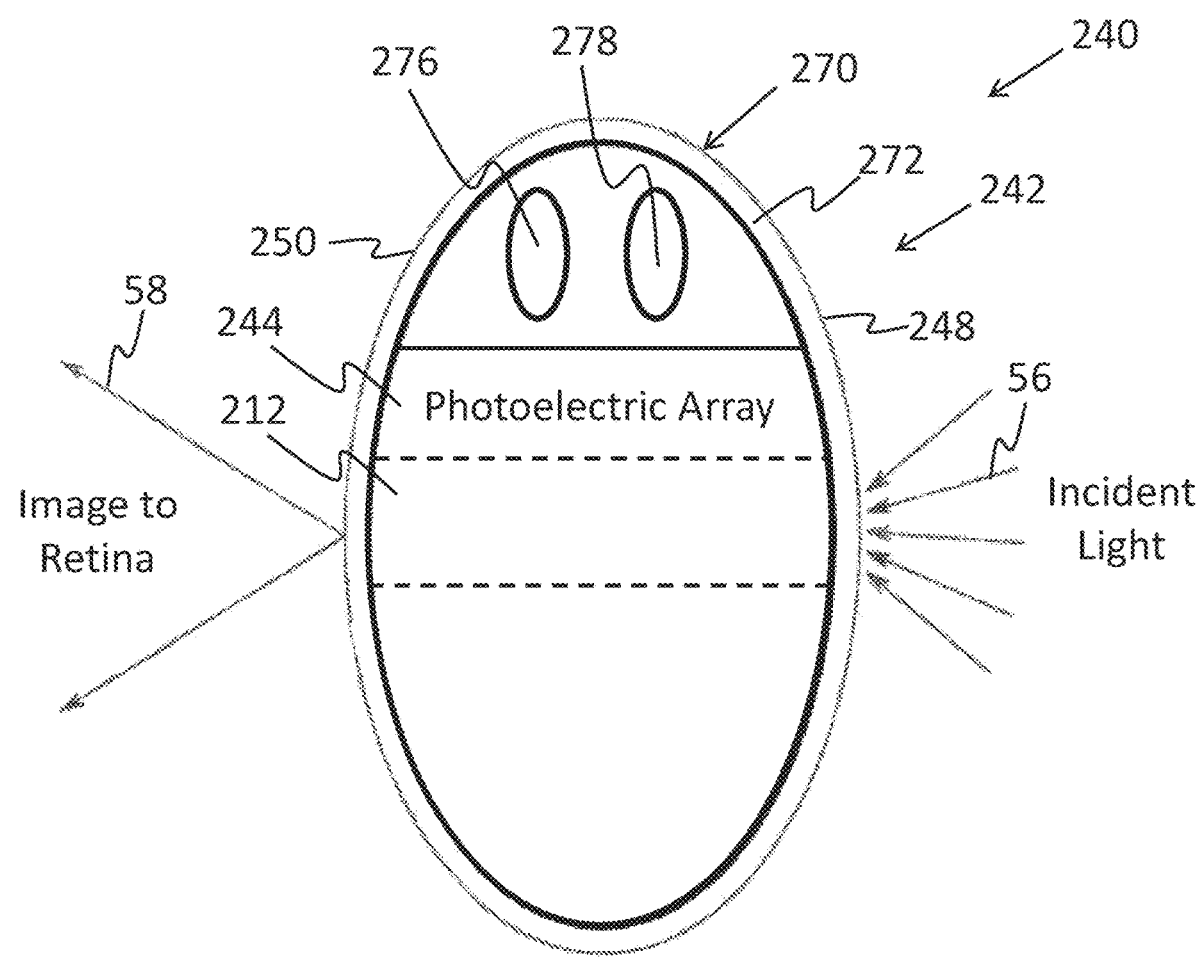
FIG. 7 is a schematic view of a removable lens device of an intraocular implant device in accordance with the present disclosure.

Referring now to FIG. 7, the RLD 240 is shown, according to some embodiments of the present disclosure. As mentioned above, the RLD 240 may include the RLD body 242. The RLD body 242 may define an anterior side 248 and a posterior side 250 (corresponding to the anterior side 48 and the posterior side 50 of the main body 42 of the device 40, as well as the anterior side 148 and the posterior side 150 of the dock body 142 of the dock 140). As discussed in greater detail below, the RLD 240 may further include various components such as the second photoelectric array 244, an optical device 212, a second power bus 276, and a second data bus 278. One or more of the aforementioned components may be disposed on the RLD body 242 as bounded by a second frame 270 that may include various components such as the second mechanical interface 272. The various aforementioned components may be positioned at any suitable location on the RLD 240, including on a common circuit board structured with one another. As discussed in greater detail below with reference to FIG. 9, when the RLD 240 is attached to the dock 140, this common circuit board formed by the components of the RLD 240 may be joined with the common circuit board structure formed by one or more components of the dock 140. In some embodiments, the components of the RLD 240 discussed herein are permanently affixed to the RLD body 242. In other embodiments, some or all of the components of the RLD 240 may be replaceably attached to the RLD body 242, such that such components may be replaced without replacing the RLD 240 itself. Furthermore, it should be appreciated that one or more components of the dock 140 may be implemented on the RLD 240, and vice-versa, depending on the implementation of the present disclosure.

As suggested above, the RLD body 242 of the RLD 240 may be bound by the second frame 270. In some embodiments, the second frame 270 defines a shape that substantially matches the shape first frame 170 of the dock 140 (as described with reference to FIG. 3). As mentioned above, the second frame 270 may include the second mechanical interface 272. As discussed in greater detail below with reference to FIG. 8, the second mechanical interface 272 may be operable to mechanically engage the corresponding first mechanical interface 172 of the dock 140 when the RLD 240 is attached to the dock 140, thereby securing the RLD 240 to the dock 140.

In some embodiments, the second photoelectric array 244 covers a portion of the surface of the anterior side 248 of the RLD body 242 and operates in a fashion similar to the first photoelectric array 144. For instance, the second photoelectric array 244 may be configured to convert the incident light 56 into electrical power and include at least one electrical output operable to transmit the electrical power to a circuit component, as discussed in greater detail below with reference to FIG. 9. Similar to the first and third photoelectric arrays 144, 174 of the dock 140, in some embodiments, the third photoelectric array may be activated and deactivated by the controller 149 as described in greater detail below with reference to FIG. 12.

In some embodiments, the optical device 212 is an electromechanical lens array. In this sense, the optical device 212 may include one or more lenses suitably configured to receive the incident light 56 as it passes through the RLD 240 (and, thus the device 40 in its entirety), adjust the received incident light until the received incident light becomes focused, and transmit the focused incident light to the retina 14 as the image 58. Further, the optical device 212 configured as the electromechanical lens array may be adjustable to improve the clarity of the image 58. For example, the lense(s) of the optical device 212 may be capable of axial movement (e.g., translation closer to the posterior side 250 or the anterior side 248) to improve the adjustment of the received light (e.g., improve the clarity of the image 58). Such axial movement may be facilitated by one or more actuators on the optical device 212, which may be controlled by the controller 149 as described in greater detail below with reference to FIGS. 8 and 13. In some embodiments, the lens array includes one or more lenses having a variable refractive index.

In other embodiments, the optical device 212 is a projector. In this sense, and as described in greater detail below with reference to FIG. 13, the optical device 212 may be configured to independently generate and transmit light to the retina 14 as some or all of the image 58 based on received image data. In other embodiments still, the optical device 212 includes both the electromechanical lens array and the projector as described above, which may be interchangeably used based on one or more input signals as described in greater detail below.

In other embodiments still, the optical device 212 is both an electromechanical lens array and a projector. In this sense, the electromechanical lens array and the projector may operate as discussed above in conjunction with one another. For instance, the input signal 166 to the controller 149 may dictate that the projector of the optical device 212 is applied in varying degrees in conjunction with the electromechanical lens array of the optical device 212. In some embodiments, the projector is inactive and positioned such that all of the incident light 56 received by the electromechanical lens array is focused and transmitted as discussed above. In other embodiments, the projector is active and positioned such that no incident light 56 is received by the electromechanical lens array, and all light received by the retina 14 is provided by the projector. In other embodiments still, the projector is active and positioned such that a portion of the incident light 56 is received and focused by the electromechanical lens array, thereby forming a portion of the light received by the retina 14, while the remaining portion of the light received by the retina 14 is provided by the projector. In other embodiments still, the projector is active and positioned such that the projector overlays light over the focused light transmitted to the retina 14 by the electromechanical lens array.

Figure 8:
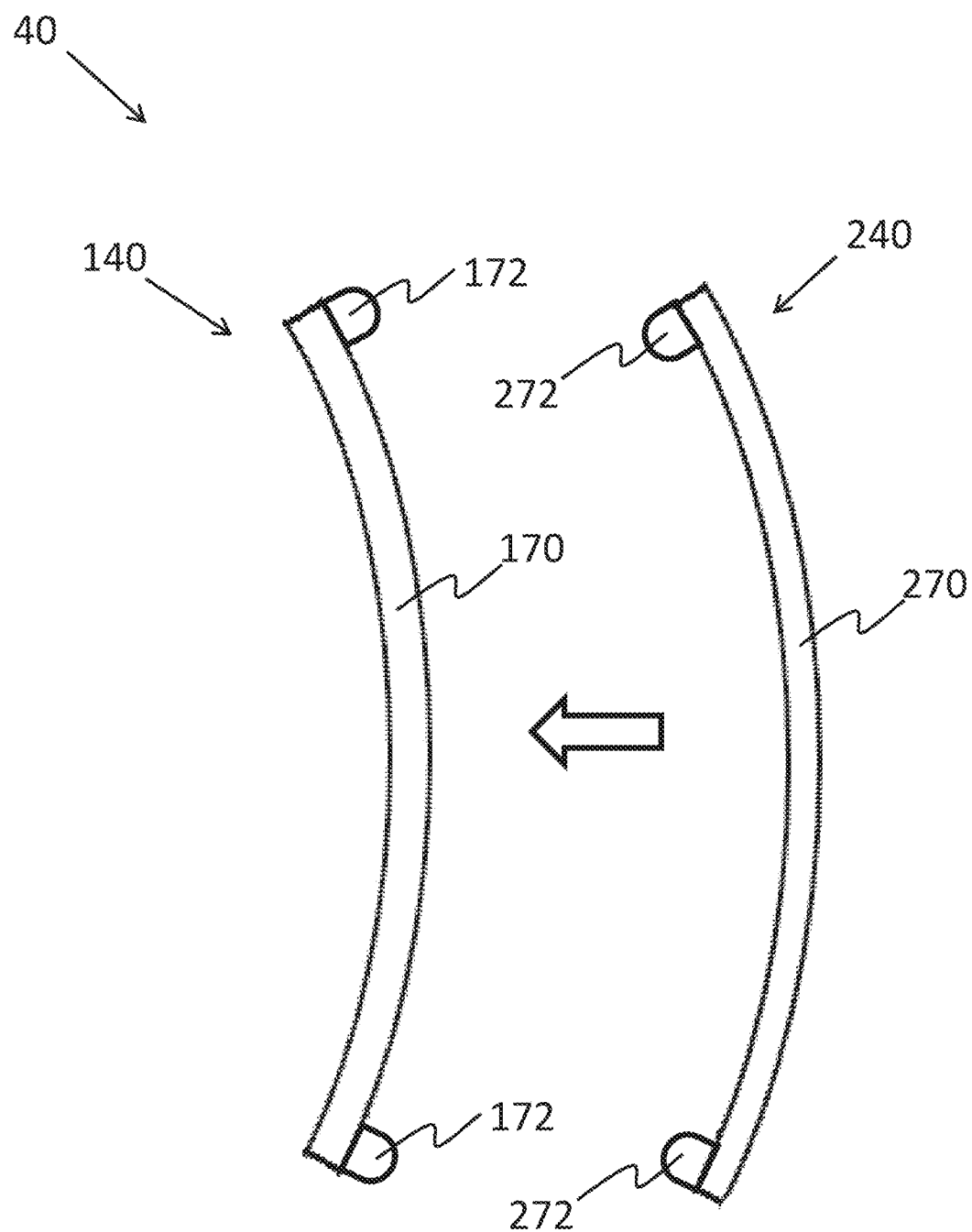
FIG. 8 is a schematic view of a frame of a dock of an intraocular implant device being positioned for replace-able attachment to a frame of a removable lens device of the intraocular implant device in accordance with the present disclosure.

Referring now to FIG. 8, the RLD 240 is shown engaging the dock 140, according to some embodiments of the present disclosure. As mentioned above with reference to FIG. 3, the first mechanical interface 172 of the dock 140 may be operable to mechanically engage the corresponding second mechanical interface 272 of the RLD 240 when the RLD 240 is attached to the dock 140. Of course, such mechanical engagement may be removable or replace-able in nature in order to remove and replace the RLD 240 when one or more components of the RLD 240 become degraded from time-to-time.

In some embodiments, the dock 140 and the RLD 240 may be sized such that when the RLD 240 is being implanted into the lens chamber 18 for replace-able attachment to the dock 140, the first frame 170 is aligned with the second frame 270 and, similarly, the first mechanical interface 172 is aligned for engagement with the second mechanical interface 272. Thus, the first mechanical interface 172 of the dock 140 may be configured to engage and retain the second mechanical interface 272 of the RLD 240.

In some embodiments, the second mechanical interface 272 forms a region of threading on the second frame 270 of the RLD 240, and the region of threading may be received by a corresponding threading formed by the first mechanical interface 172 of the dock 140. In other words, the RLD 240 may be "screwed" onto the dock 140. In other embodiments, the second mechanical interface 272 forms a number of press-fit members extending from the second frame 270, and the press-fit members may be received by a corresponding number of press-fit retainers formed by the first mechanical interface 172 of the dock 140. In other words, the RLD 240 may be "press-fit" or "snap-fit" onto the dock 140. In other embodiments still, the first mechanical interface 172 may be configured for magnetic engagement with the second mechanical interface 272. In even other embodiments, the first and/or second mechanical interfaces 172, 272 may include one or more electromechanical components configured for actuation in order to secure the engagement discussed herein. As a first example, the first mechanical interface 172 may include a series of arms or hooks that, when the dock 140 is in contact or close proximity with the RLD 240, move to engage a series of corresponding retainers defined by the second mechanical interface 272 (or vice-versa). As a second example, such connection may be made via a pin-and-socket configuration. Such electromechanical engagement is discussed in greater detail below with reference to FIG. 9. In general, the first and second mechanical interfaces 172, 272 may be arranged in any suitable manner for replace-able attachment of the RLD 240 to the dock 140.

Figure 9:
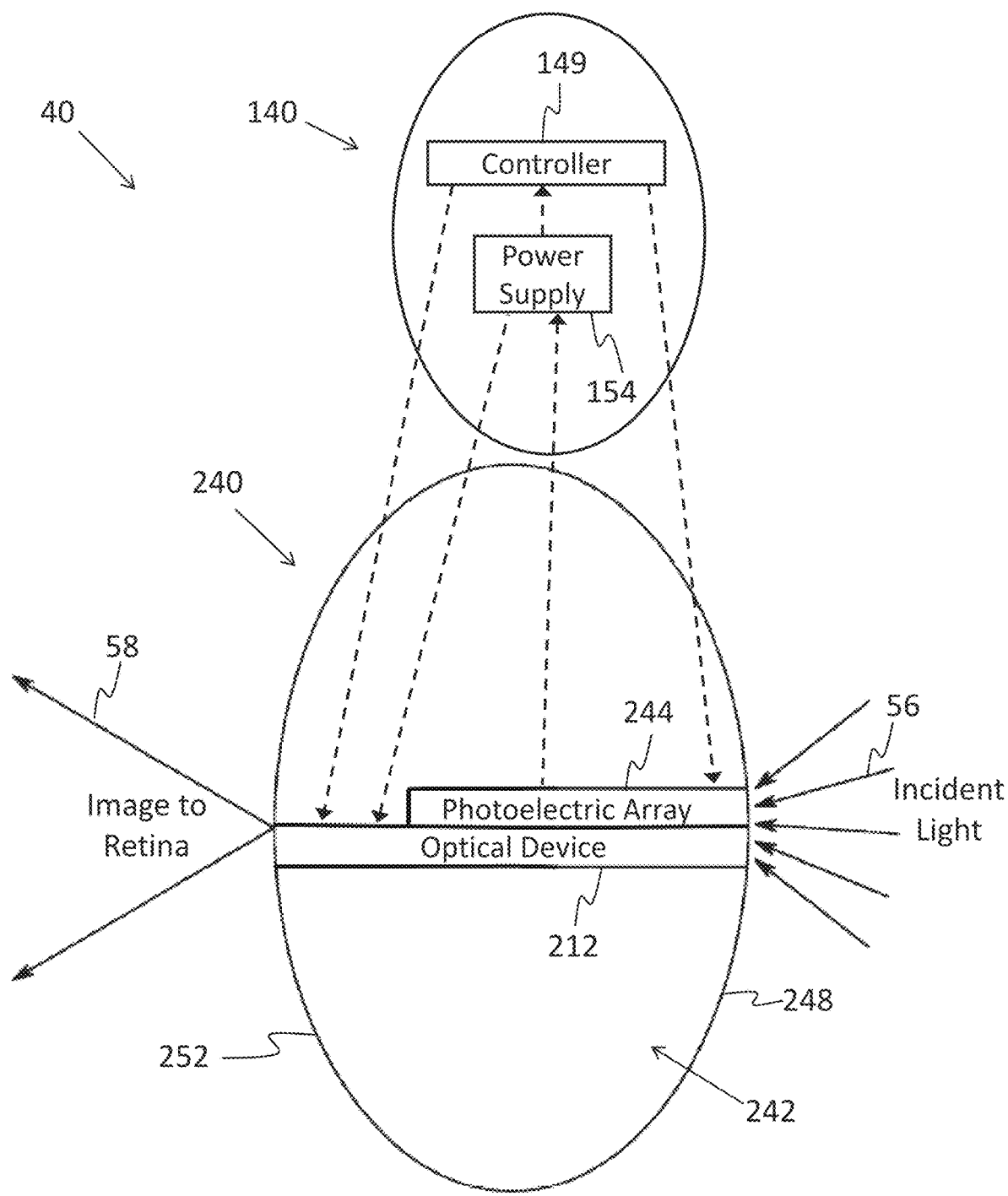
FIG. 9 is a schematic view of a removable lens device of an intraocular implant device engaged with a dock of an intraocular implant device in accordance with the present disclosure.

Referring now to FIG. 9, operation of the device 40 (e.g., each of the RLD 240 and the dock 140 when the RLD 240 is attached to the dock 140) is shown, according to some embodiments of the present disclosure.

Figure 10:
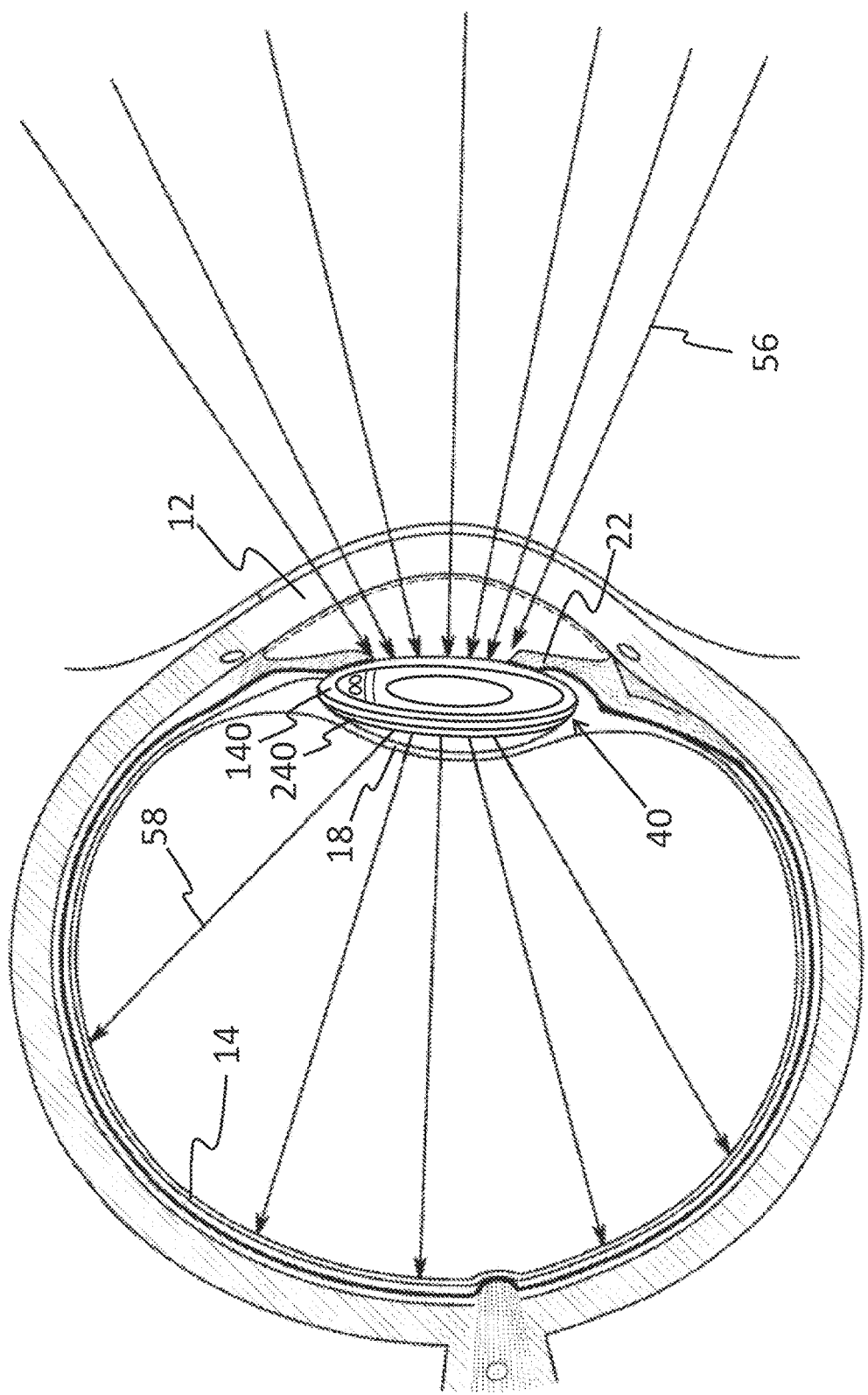
FIG. 10 is a schematic view of an intraocular implant device within the lens chamber of an eye in accordance with the present disclosure.

As mentioned above, the first power bus 176 and/or the first data bus 178 of the dock 140 may be configured to exchange power and/or data with various components of the RLD 240 when the RLD 240 is attached to the dock 140. In particular, such exchanges may be facilitated by the corresponding second power bus 276 and/or the second data bus 278 of the RLD 240. For instance, when the RLD 240 is attached to the dock 140 (as described above with reference to FIG. 8 and further depicted with reference to FIGS. 10-11), the first and second power busses 176, 276 may be in contact or otherwise aligned and therefore operable to exchange electrical power (forming a power junction). Similarly, the first and second data busses 178, 278 may be in contact or otherwise aligned and therefore operable to exchange one or more data inputs (forming a data junction). In other words, as facilitated by the power junction formed by the first and second power busses 176, 276 and the data junction formed by the first and second data busses 178, 278, the various aforementioned components of the dock 140 may form a common circuit board structure with the various components of the RLD 240.

As described herein, the RLD 240 and the dock 140 may be suitably sized for engagement, and various components of the dock 140 and the RLD 240 may be particularly located on their respective dock and RLD bodies 142, 242 for interaction when the dock 140 is engaged with the RLD 240. Accordingly, it should be appreciated that the illustration shown, as well as other depictions of the dock 140 and RLD 240 herein, are merely exemplary for the purposes of describing the device 40 provided for herein.

As mentioned above with reference to FIG. 4, the power supply 154 of the dock 140 may store electrical power generated by one or more components of the dock 140 (e.g., the first and/or third photoelectric arrays 144, 174) for later use by one or more other circuit components (e.g., the controller 149, the receiver 152). Further, the power supply 154 may be recharged by one or more components of the RLD 240 when the RLD 240 is attached to the dock 140. For example, when the RLD 240 is attached to the dock 140, the second photoelectric array 244 may be coupled with the power supply 154 of the dock 140 (via the power junction formed by the first and second power busses 176, 276). Accordingly, the power supply 154 may be recharged by the second photoelectric array 244 when the RLD 240 is attached to the dock 140.

Depending on the implementation, when the RLD 240 is attached to the dock 140, the power supply 154 may be continuously recharging as additional incident light 56 is received by the first, second, and/or third photoelectric arrays 144, 244, 174. As described in greater detail below with reference to FIG. 12, however, only some of the first, second, and third photoelectric arrays 144, 244, 174 may be used to recharge the power supply 154 when the RLD 240 is attached to the dock 140, in order to optimize efficiency of the device 40, among other concerns. In turn, the power supply 154 may be simultaneously distributing electrical power to other circuit components of the device 40. For example, in addition to supplying power to the receiver 152, the controller 149 and other components of the dock 140 as described above, when the RLD 240 is attached to the dock 140, the power supply 154 may be configured to further distribute electrical power to various components of the RLD 240, such as the optical device 212 (via the power junction formed by the first and second power busses 176, 276).

As mentioned above, the controller 149 may be in communication with and/or control one or more of the various components of the dock 140. Further, as discussed in greater detail below with reference to FIGS. 12-13, when the RLD is attached to the dock 140, the controller 149 may be in communication with and/or control one or more of the various components of the device 40 in its entirety (via the data junction formed by the first and second data busses 178, 278), such as the second photoelectric array 244 and the optical device 212.

Figure 11:
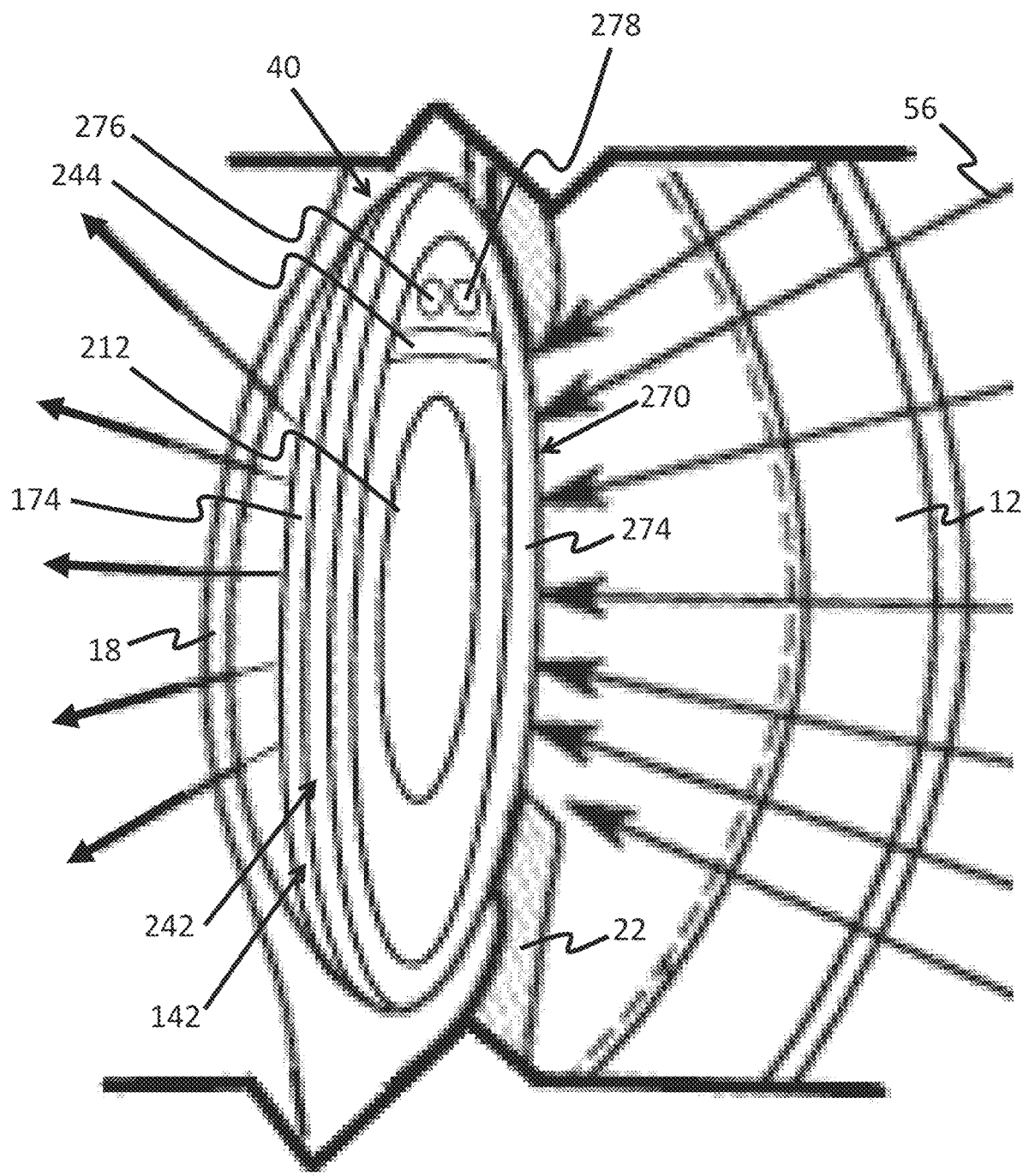
FIG. 11 is a detailed schematic view of an intraocular implant device within the lens chamber of an eye in accordance with the present disclosure.
Figure 12:
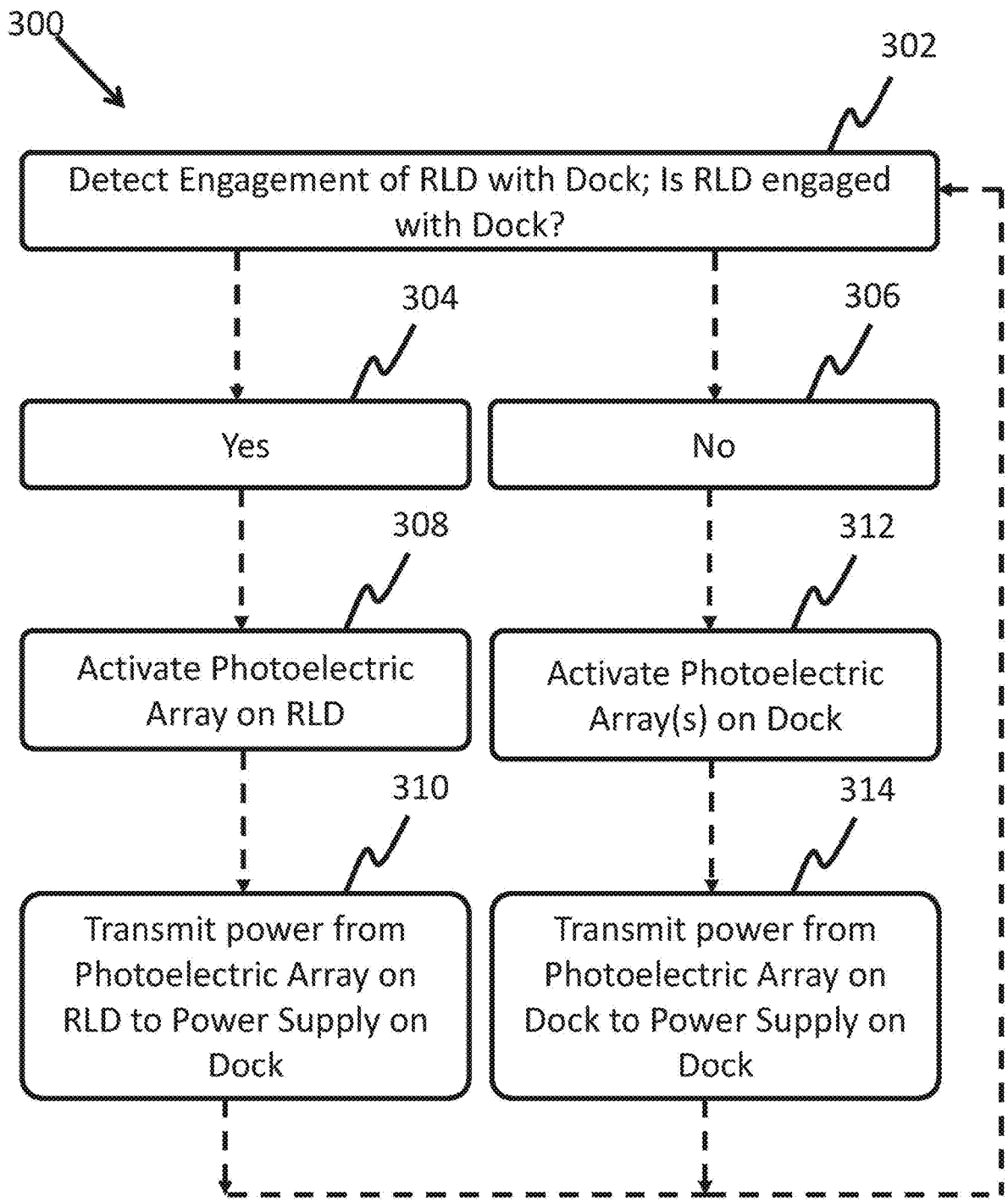
FIG. 12 is a flow diagram illustrating operation of a controller of an intraocular implant device in accordance with the present disclosure.

Referring now to FIGS. 11-12, the RLD 240 is shown inserted into the lens chamber 18 of the eye 10 and attached to the dock 140, according to some embodiments of the present disclosure. In other words, FIGS. 11-12 depicts the device 40 in its entirety inserted into the lens chamber 18 of the eye 10. For example, as mentioned above, the dock 140 may be inserted into the empty lens chamber 18 as discussed above with reference to FIGS. 5-6. In turn, the RLD 240 may be inserted into the empty lens chamber 18 in order to engage the dock 140. As mentioned above, in cases of a conventional intraocular implant device inserted into the eye to replace a damaged or occluded lens, the device may degrade over time, typically requiring additional highly invasive surgical procedures. Advantageously, however, any components of the device 40 subject to typical degradation may be disposed on the RLD 240 which, as described herein, may be easily replaceable with less invasive surgery.

As mentioned above, the dock 140 may include the orifice 112. In some embodiments, when the RLD 240 is attached to the dock 140, the optical device 212 is aligned with the orifice 112. For instance, in embodiments where the optical device 212 is an electromechanical lens array, the optical device 212 may be aligned with the orifice 112 such that the incident light 56 passes through (and may be adjusted by) the optical device 212 as discussed above, and proceeds to pass through the orifice 112 unobstructed in order to be transmitted to the retina 14 as the image 58. Alternatively, in embodiments where the optical device 212 is a projector, the optical device 212 may be aligned with the orifice 112 such that the optical device 212 may independently generate and transmit light through the orifice to the retina 14 as some or all of the image 58 based on received image data. In some embodiments, the lens array is configured to correct both near and far sightedness, and such correction is independently controllable via the controller. Such embodiments may be referred to as a dual mode lens array.

Referring now to FIG. 12, a control loop 300 for operation of the controller 149 of the dock 140 is shown, according to some embodiments of the present disclosure. The control loop 300 illustrates the selective operation of the first and third photoelectric arrays 144, 174 of the dock 140, as well as the second photoelectric array 244 of the RLD 240. For instance, as mentioned above, the first, second, and third photoelectric arrays 144, 244, 174 may be activated and deactivated as controlled by the controller 149.

At a first step 302 of the control loop 300, the controller 149 may detect engagement of the RLD 240 with the dock 140. As an example, and as discussed above, when the RLD 240 is attached to the dock 140, the first and second data busses 178, 278 may form a data junction. The controller 149 may be configured to detect when such a data junction is performed. As another example, the first and/or second mechanical interfaces 172, 272 of the dock 140 and the RLD 240 (respectively) may include sensors in communication with the controller 149, thereby allowing the controller 149 to detect when the RLD 240 is attached to the dock 140. Accordingly, the controller 149 may determine whether the RLD 240 is attached to the dock 140.

If the controller 149 determines that the RLD 240 is attached to the dock 140 (as depicted with reference to FIGS. 7-8), via a decision 304, the first power bus 176 may activate the second photoelectric array 244 on the RLD 240 in a step 308, thereby initiating operation of the second photoelectric array 244 to convert the incident light 56 to electrical power and transmit the electrical power to the power supply 154 in a step 310 of the control loop 300. For instance, when the RLD 240 is attached to the dock 140, the RLD body 242 of the RLD 240 may cover or obscure the portion of the dock body 142 of the dock 140 on which the first photoelectric array 144 is located, thereby preventing all or most of the incident light 56 from reaching the first photoelectric array 144. Conversely, when the RLD 240 is attached to the dock 140, the second photoelectric array 244 may be in position to efficiently receive the incident light 56 and convert the incident light 56 to electrical power.

Further, in the step 308, the controller 149 may deactivate the first photoelectric array 144 in the step 308, thereby ceasing operation of the second photoelectric array 244 to convert the incident light 56 to electrical power and transmit the electrical power to the power supply 154. Advantageously, this may conserve power that may otherwise be inefficiently expended through operation of the first photoelectric array 144 when covered by the RLD body 242.

Moreover, the controller 149 may similarly activate the (or not deactivate the already activated) third photoelectric array 174 on the dock 140. For instance, as mentioned above, the third photoelectric array 174 may be positioned on the first frame 170. Therefore, when the RLD 240 is attached to the dock 140, the RLD body 242 may cover the first photoelectric array 144 is located, while leaving the third photoelectric array 174 uncovered. In some embodiments, the third photoelectric array 174 is deactivated when the RLD 240 is not attached to the dock 140, due to the more advantageous position of the first photoelectric array 144 for receiving the incident light 56. In such cases, the second photoelectric array may be activated at the step 308 to improve the amount of power being transmitted to the power supply 154. In other embodiments, the third photoelectric array is simply always activated (e.g., regardless of whether the RLD 240 is attached to the dock 140), in which case the controller 149 may not make any changes regarding operation of the third photoelectric array 174 when the RLD 240 is attached to the dock 140. Thus, depending on the implementation, activation of the third photoelectric array 174 may be provided as an auxiliary or additional source of power for charging the power supply 154 when the RLD 240 is attached to the dock 140.

If the controller 149 determines that the RLD 240 is not attached to the dock 140 (as depicted with reference to FIGS. 4-5), via a decision 306, the controller 149 may activate the first photoelectric array 144, thereby initiating operation of the first photoelectric array 144 to convert the incident light 56 to electrical power and transmit the electrical power to the power supply 154 in a step 314 of the control loop 300. For instance, when the RLD 240 is not attached to the dock 140, the first photoelectric array 144 may not be covered by the RLD body 242 of the RLD 240, and may otherwise be required for recharging the power supply 154. The second photoelectric array 244, of course, may be configured to be deactivated whenever there is no connection with the controller 149 and/or the power bus 154 via the power and/or data junctions formed by the first and second power busses 176, 276 and/or the first and second data busses 178, 278.

Further, in the step 308, the controller 149 may similarly activate the third photoelectric array 174 in the step 308 (if it was previously deactivated, depending on the implementation), thereby initiating operation of the third photoelectric array 174 to convert the incident light 56 to electrical power and transmit the electrical power to the power supply 154 in the step 314.

After completion of the step 310 or the step 314, the control loop 300 returns to the step 302, where the controller repeats the detection of engagement between the RLD 240 and the dock 140 (and the ensuing steps as discussed above), thereby forming a continuous control loop for directing the operation and power supply functions of the first, second, and third photoelectric arrays 144, 244, 174 for charging the power supply 154.

Figure 13:
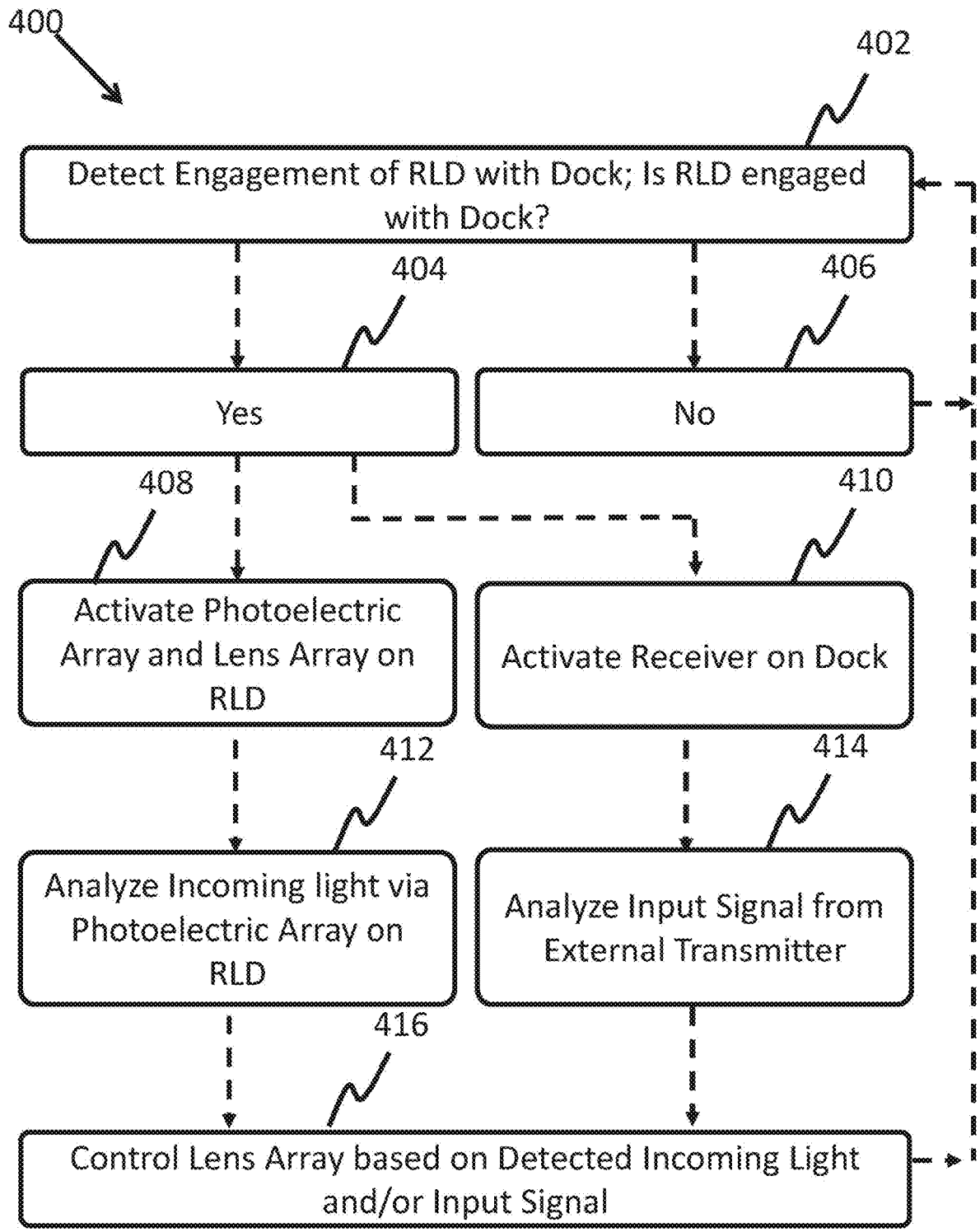
FIG. 13 is a flow diagram illustrating operation of a controller of an intraocular implant device, according to further embodiments of the present disclosure.

Referring now to FIG. 13, a control loop 400 for operation of the controller 149 of the dock 140 is shown, according to some embodiments of the present disclosure. The control loop 400 illustrates the selective operation of the optical device 212 and second photoelectric array 244 of the RLD 240, as well as the receiver 152 of the dock 140. In some embodiments, the control loop 300 discussed above with reference to FIG. 12 may be simultaneously conducted (regarding activation and/or deactivation of the first, second, and third photoelectric arrays 144, 244, 174).

At a first step 402 of the control loop 400, the controller 149 may detect engagement of the RLD 240 with the dock 140 as discussed above regarding the step 302 of the control loop 300 depicted with reference to FIG. 12.

If the controller 149 determines that the RLD 240 is attached to the dock 140, via a decision 404, the controller 149 may activate the second photoelectric array 244 on the RLD 240 and deactivate the first photoelectric array 144 on the dock 140 in a step 408, as discussed above regarding the step 308 of the control loop 300. Further, the controller 149 may activate the optical device 212 in the step 408. For instance, as discussed above, the optical device 212 may be an electromechanical lens array and/or a projector (depending on the implementation), as discussed above with reference to FIG. 7. In such cases, the controller 149 may activate the optical device 212 to initiate operation as discussed above, and as expanded upon below.

In some embodiments, when the controller determines that the RLD 240 is attached to the dock 140 via the decision 404, the controller 149 may further activate the receiver 152 on the dock 140 at a step 410. As an example, the activated receiver 152 may receive the digital input signal(s) 166 from the external transmitter 164. In embodiments where the optical device 212 is an electromechanical lens array or a projector, the digital input signals 166 from the external transmitter 164 may be used by the controller 149 to control the optical device 212 as discussed below.

At a step 412 of the control loop 400 in response to the step 408, the controller 149 may analyze the incoming light being received by the device 40. Depending on the implementation, the controller 149 may analyze the amount of incident light 56 via the activated second photoelectric array 244 (and, in some cases, the third photoelectric array 174). As mentioned above, the second and third photoelectric arrays 244, 174 are configured to convert the received incident light 56 into electrical power. In some embodiments, the second and third photoelectric arrays 244, 174 may be configured to directly communicate the amount of the incident light 56 being received by the device 40 as part of this function to the controller 149. In other embodiments, given that the second and third photoelectric arrays 244, 174 are configured to transmit the generated electrical power to the power supply 154, the controller 149 may receive an indication from the power supply 154 as to how much power has been received by the power supply 154 for recharging the power supply 154, and similarly determine the amount of incident light 56 being received by the device 40. Depending on the implementation, the controller 149 may analyze the amount of incident light 56 in order to determine various operational changes to be made in order to optimize the function of the optical device 212, as discussed below.

At a step 414 of the control loop 400 in response to the step 410, the controller 149 may receive and analyze the input signal(s) 166 received by the receiver 152 from the external transmitter 164. In some embodiments, the input signal 66 includes information associated with the lighting conditions of the surrounding environment. For example, the external transmitter 164 may be, or be in communication with, an external monitor (e.g., a camera device, video recording device, or a suitable light detector) configured to determine the amount of light in the surrounding environment. In other embodiments, the input signal 66 includes image data associated with the surrounding environment. For example, the external transmitter 164 may be, or be in communication with, an external camera or video recording device that records image data regarding the surrounding environment within the field of vision of the eye 10. In other embodiments still, the input signal 166 includes one or more manual controls regarding operation of the optical device 212 (e.g., manual adjustments to correct near-sightedness or far-sightedness). Depending on the implementation, the controller 149 may analyze the input signal(s) 166 in order to determine various operational changes to be made in order to optimize the function of the optical device 212, as discussed below.

At a step 416 of the control loop 400 in response to the steps 412 and 414, the controller 149 may control the optical device 212 based on the analysis of the incident light 56 (conducted at the step 412) and the analysis of the input signal(s) 166 (conducted at the step 414). In other embodiments, the controller 149 only controls the optical device 212 based on the analysis of the incident light 56. In other embodiments still, the controller 149 only controls the optical device 212 based on the input signal(s) 166.

As discussed herein, the first and second data busses 178, 278; and the first and second power busses 176, 276 are generally discussed as configured for providing a data junction and a power junction under a bus architecture. Of course, in further embodiments of the present disclosure, such data junction and power conjunction may be provided under a point-to-point architecture, or some combination of a bus architecture and a point-to-point architecture.

Figure 14:
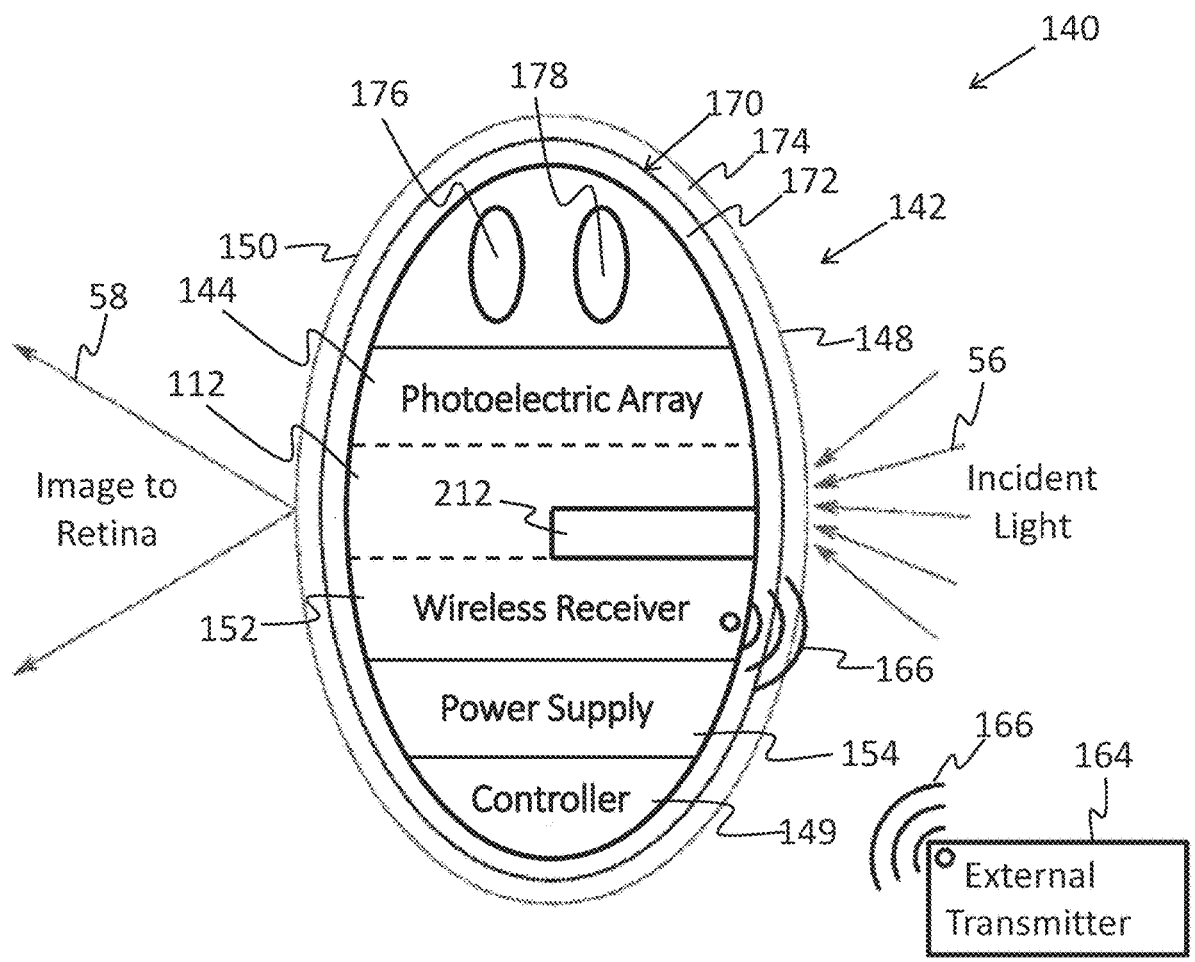
FIG. 14 is a schematic view of an intraocular lens docking station (dock) of an intraocular implant device where an optical device is disposed on the dock, according to further embodiments of the present disclosure.

Referring now to FIG. 14, the dock 140 is shown, according to further embodiments of the present disclosure. In some embodiments, the optical device 212 is disposed on the dock 140 (e.g., replaceably attached to the dock 140), particularly in cases where the optical device 212 is a projector. In this sense, the projector of the optical device 212 may be mounted on the dock 140, and may be configured to swivel into position when activated as discussed herein.

Figure 15:
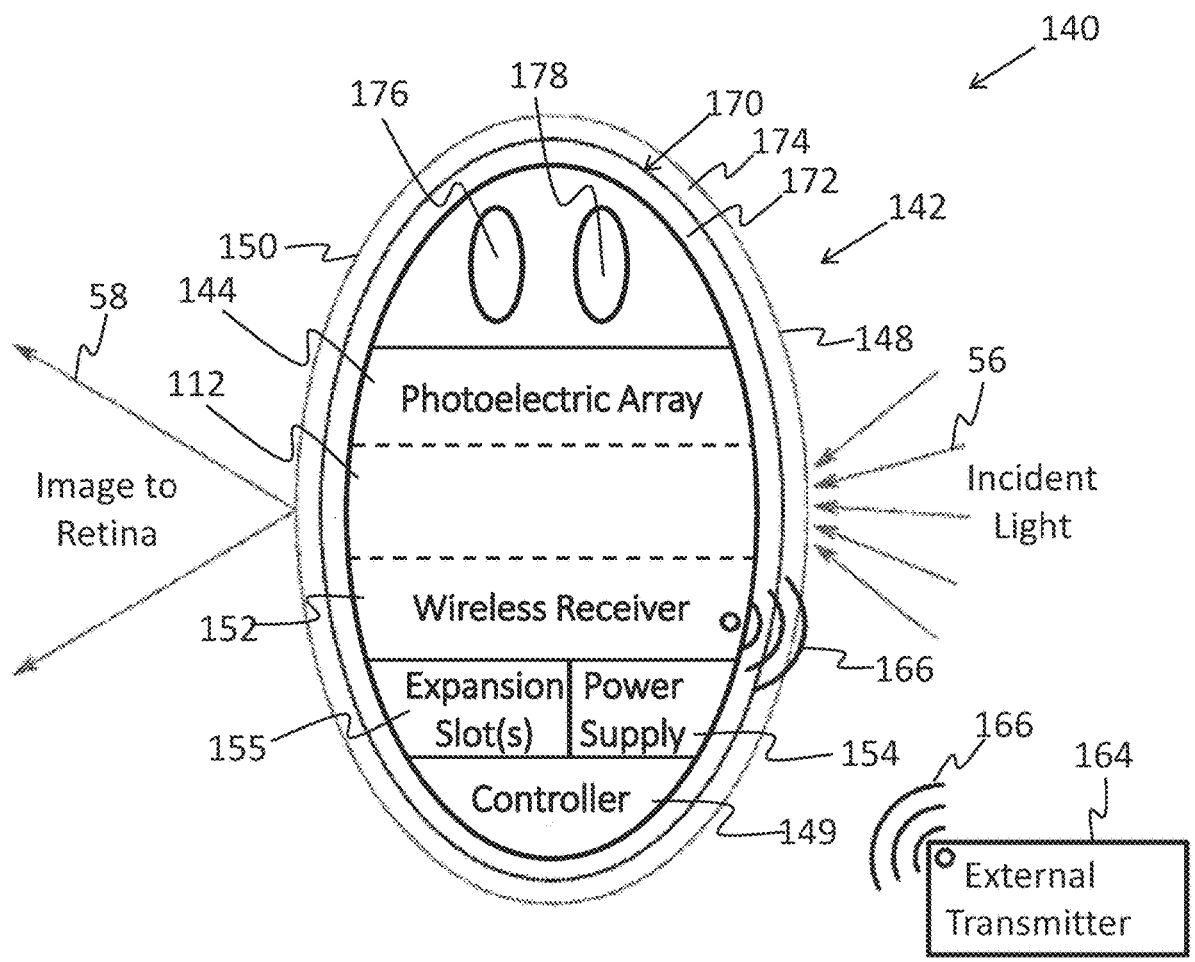
FIG. 15 is a schematic view of an intraocular lens docking station (dock) of an intraocular implant device where one or more expansion slot(s) are disposed on the dock, according to further embodiments of the present disclosure.

Referring now to FIG. 15, the dock 140 is shown, according to further embodiments of the present disclosure. In some embodiments, The dock 140 includes one or more expansion slot(s) 155 disposed on the dock body 142. The expansion slot(s) 155 may be configured to receive one or more additional devices configured to provide additional functional or sensing mechanisms to the device 40. Such additional devices may thus be replaceably attached to the dock 140. As a first example, the expansion slot(s) 155 may be configured to receive a glucose monitor. As a second example, the expansion slot(s) 155 may be configured to receive an intraocular pressure ("IOP") monitor. Depending on the implementation, such glucose monitor, IOP monitor, or any other suitable mechanism may be configured to detect conditions and provide control signals for directing the function of the device 40 as discussed herein. In alternative embodiments, the expansion slot(s) 155 are disposed on the RLD 240.

Figure 16:
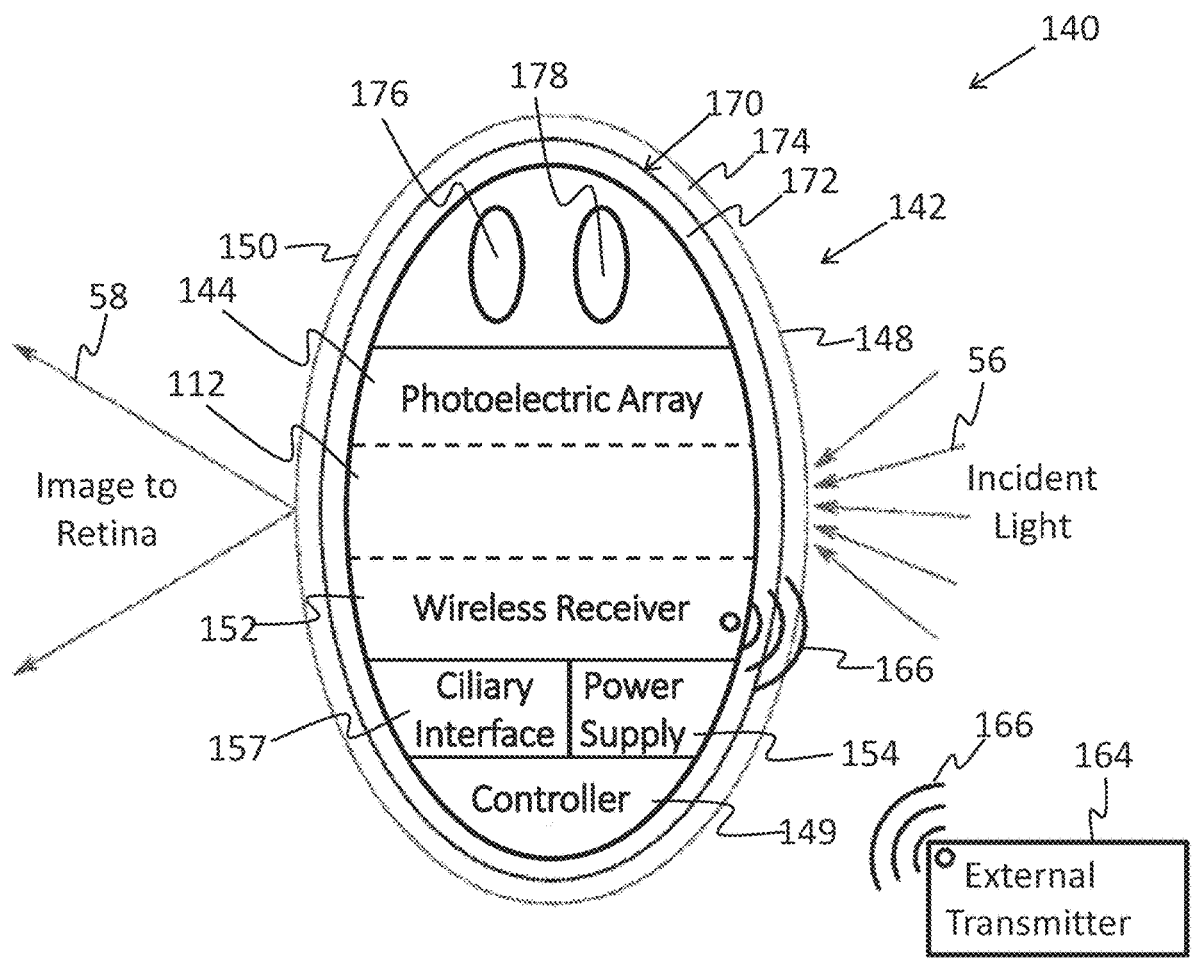
FIG. 16 a schematic view of an intraocular lens docking station (dock) of an intraocular implant device where the dock includes a ciliary interface module, according to further embodiments of the present disclosure.

Referring now to FIG. 16, the dock 140 is shown, according to further embodiments of the present disclosure. In some embodiments, the dock 140 includes a ciliary interface module 157 disposed on the dock body 142. In other embodiments, the ciliary interface module 157 is a component of the controller 149. As mentioned above, the receiver 152 may be configured to receive the input signal 166 from the external transmitter 164, and the receiver 152 may provide the input signal 166 to the controller 149 in order to control one or more components of the device 40. In further embodiments, the ciliary interface module 157 may (as either transmitting control signals to the controller 149 or as a component of the controller 149) provide control signals that either replace, or are interpreted in conjunction with, the input signals 166.

The ciliary interface module 157 may include (or be in communication with) mechanical, electrical, chemical, or any other suitable sensing elements to detect one or more conditions of the eye 10. In particular, such sensing elements may detect one or more conditions or signals (such as electrical signals) of a ciliary body of the eye 10, including a ciliary muscle of the ciliary body. Such sensing elements may detect conditions of the eye 10 such as pressure and movement in order to provide control signals as discussed above. For example, such sensing elements may be disposed in the eye 10. In operation, the brain may naturally determine necessary adjustments to the ciliary body in order to provide needed accommodation in the focus of the eye 10. In turn, the brain may send electrical signals to the ciliary body. Such signals may be detected by the aforementioned sensing elements in the form of pressure alterations or movements of the ciliary body, which may then be communicated to components of the device 40 in order to provide the adjustments and/or accommodations discussed herein. Additionally, even after the onset of presbyopia, the brain may continue to send ghost neural accommodation signals to the vicinity of the ciliary muscle. In some embodiments, an electrode may be placed to sense the neural accommodation signals to be used by an intraocular device in the eye for artificial accommodation. In some embodiments, a ciliary interface module 157 receives, analyzes and/or processes such neural accommodation signals and provides the signal, or a processed form of the signal, to the controller.

Figure 17:
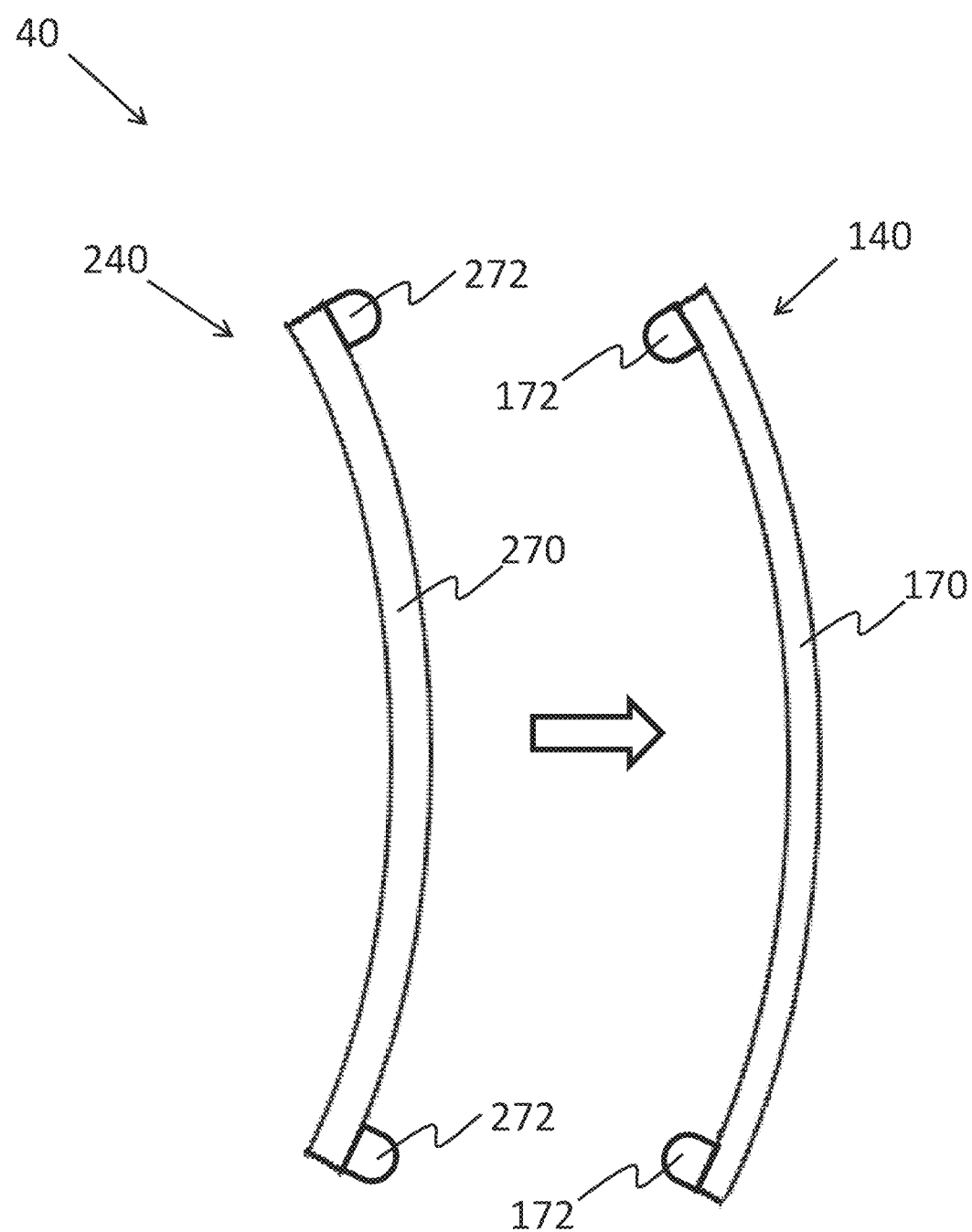
FIG. 17 is a schematic view of a frame of a dock of an intraocular implant device being positioned for replace-able attachment from the rear of a frame of a removable lens device of the intraocular implant device, according to further embodiments of the present disclosure.

Referring now to FIG. 17, the RLD 240 is shown being attached to the dock 140, according to further embodiments of the present disclosure. As depicted with reference to FIG. 8, the RLD 240 may generally be attached to the dock 140 on the anterior side 148 of the dock body 142. In further embodiments, and as shown, the RLD 240 may be attached to the dock 140 on the posterior side 150 of the dock body 142.

In further embodiments, the apparatus includes a dock 140 having an annular shape with an opening in the center and a first photoelectric array positioned circumferentially around the opening facing away from the retina. A power supply, controller and receiver are disposed on the dock 140. A RLD 240 is disposed in the opening on the dock, and the diameter of the RLD 240 does not extend radially past the perimeter of the opening on the dock 140. In such embodiments, the dock 140 operates as a frame, and no part of the RLD 240 obscures the frame formed by dock 140 from the front of the frame facing away from the retina such that the front of the dock 140 may be exposed to light.

Thus, although there have been described particular embodiments of the present invention of a new and useful INTRAOCULAR LENS DOCKING STATION, it is not intended that such references to particular embodiments be construed as limitations upon the scope of this invention.

What is claimed is:

1. An intraocular implant device, comprising:
   a dock shaped for positioning inside a lens chamber of an eye, wherein the dock includes a dock body having an anterior side positioned to face a cornea of the eye and a posterior side positioned to face a retina of the eye, a first frame disposed on the dock body, and a power supply and a controller disposed on the dock body on the first frame; and
   a removable lens device (RLD) shaped for positioning inside the lens chamber of the eye, wherein the RLD includes an RLD body having an anterior side positioned to face the cornea of the eye and a posterior side positioned to face the retina of the eye, a second frame disposed on the RLD body, and an electromechanical lens array disposed on the RLD body on the second frame, the electromechanical lens array including one or more lenses configured to receive incident light through the cornea, convert the incident light into a focused image, and transmit the focused image to the retina,
   wherein the second frame of the RLD is configured to replaceably attach to the first frame of the dock, and
   wherein the electromechanical lens array is configured to receive electrical power from the power supply of the dock when the RLD is attached to the dock and to receive one or more control signals from the controller when the RLD is attached to the dock, such that the electromechanical lens array is operable to adjust an axial position of the one or more lenses based on the one or more control signals to increase a clarity of the focused image.

2. The implant device of claim 1, further comprising:
   a first power bus and a first data bus disposed on the dock body on the first frame, the first power bus being in communication with the power supply, and the first data bus being in communication with the controller,
   a second power bus and a second data bus disposed on the RLD body on the second frame, the second power bus and the second data bus being in communication with the electromechanical lens array of the RLD, and
   wherein when the RLD is attached to the dock, the first power bus is in communication with the second power bus, and the first data bus is in communication with the second data bus.

3. The implant device of claim 2, further comprising:
   a receiver or transceiver disposed on the dock body on the first frame, the receiver or transceiver configured to wirelessly receive an input signal from an external transmitter and transmit the input signal to the controller, wherein the controller is configured to provide the one or more control signals to the electromechanical lens array based on the input signal.

4. The implant device of claim 2, further comprising:
a first photoelectric array disposed on the dock body on the first frame and in communication with the power supply, wherein the first photoelectric array is operable to receive the incident light through the cornea, convert the incident light into electrical power, and transmit the electrical power to the power supply for charging the power supply.

5. The implant device of claim 4, further comprising:
a second photoelectric array disposed on the RLD body on the second frame, wherein when the RLD is attached to the dock, the second photoelectric array is in communication with the power supply of the dock via the first and second power busses,
and the second photoelectric array is operable to receive the incident light through the cornea, convert the incident light into electrical power, and transmit the electrical power to the power supply for charging the power supply, and
wherein the controller is configured to selectively activate the first and second photoelectric arrays via the first and second data busses and the first and second power busses, such that the controller activates the first photoelectric array to convert the incident light into electrical power in response to the RLD becoming disengaged from the dock, and the controller activates the second photoelectric array to convert the incident light into electrical power in response to the RLD becoming attached to the dock.

6. The implant device of claim 5, further comprising:
a third photoelectric array disposed on the dock body on the first frame and in communication with the power supply, wherein the third photoelectric array is operable to receive the incident light through the cornea, convert the incident light into electrical power, and transmit the electrical power to the power supply for charging the power supply,
wherein the controller is further configured to determine an amount of the incident light being received by the second photoelectric array in response to the RLD being attached to the dock, and
wherein the controller is further configured to provide the one or more control signals to the electromechanical lens array based on the determined amount of the incident light being received by the second photoelectric array.

7. The implant device of claim 6, wherein at least one of the first, second and third photoelectric arrays includes a multi-junction photoelectric array.

8. The implant device of claim 1, wherein at least one of the dock body and the RLD body are foldable.

9. The implant device of claim 1, wherein at least one of the dock body and the RLD body are segmented.

10. The implant device of claim 1, wherein one or more lenses of the electromechanical lens array include a variable refractive index lens.

11. The implant device of claim 1, further comprising a ciliary interface module including at least one sensor configured to detect a signal from a ciliary body of the eye.

12. The implant device of claim 1, wherein the electromechanical lens array is configured to operate in a dual mode to correct both near-sightedness and far-sightedness.

13. The implant device of claim 1, further comprising an antenna.

14. An intraocular implant device, the implant device comprising:

a dock shaped for positioning inside a lens chamber of an eye, wherein the dock includes a dock body having an anterior side positioned to face a cornea of the eye and a posterior side positioned to face a retina of the eye, a first frame disposed on the dock body, and a power supply and a controller disposed on the dock body on the first frame; and a removable lens device (RLD) shaped for positioning inside the lens chamber of the eye, wherein the RLD includes an RLD body having an anterior side positioned to face the cornea of the eye and a posterior side positioned to face the retina of the eye, a second frame disposed on the RLD body, and a projector disposed on the RLD body on the second frame, wherein the second frame of the RLD is configured to replaceably attach to the first frame of the dock, such that the RLD is replaceably attached to the dock, and wherein the projector is configured to receive electrical power from the power supply of the dock when the RLD is attached to the dock and to receive one or more control signals from the controller when the RLD is attached to the dock, such that the projector is operable to emit photons onto the retina in a pattern representative of focused image data based on the one or more control signals.

15. The implant device of claim 14, further comprising:
a first power bus and a first data bus disposed on the dock on the first frame, the first power bus being in communication with the power supply, and the first data bus being in communication with the controller; and
a second power bus and a second data bus disposed on the RLD on the second frame, the second power bus and the second data bus being in communication with the projector of the RLD,
wherein when the RLD is attached to the dock, the first power bus is in communication with the second power bus, and the first data bus is in communication with the second data bus.

16. The implant device of claim 15, further comprising:
a receiver or transceiver disposed on the dock body on the first frame, the receiver or transceiver configured to wirelessly receive an input signal from an external transmitter and transmit the input signal to the controller,
wherein the controller is further configured to provide the one or more control signals to the projector based on the input signal.

17. The implant device of claim 16, further comprising:
a first photoelectric array disposed on the dock body on the first frame and in communication with the power supply, wherein the first photoelectric array is operable to receive the incident light through the cornea, convert the incident light into electrical power, and transmit the electrical power to the power supply for charging the power supply.

18. The implant device of claim 17, further comprising:
a second photoelectric array disposed on the RLD body on the second frame, wherein when the RLD is attached to the dock, the second photoelectric array is in communication with the power supply of the dock via the first and second power busses,
wherein when the RLD is attached to the dock, the second photoelectric array is operable to receive the incident light through the cornea, convert the incident light into electrical power, and transmit the electrical power to the power supply for charging the power supply, and wherein the controller is configured to selectively activate the first and second photoelectric arrays via the first and second data busses and the first and second power busses, such that the controller activates the first photoelectric array to convert the incident light into electrical power in response to the RLD becoming disengaged from the dock, and the controller activates the second photoelectric array to convert the incident light into electrical power in response to the RLD becoming attached to the dock.

19. The implant device of claim 18, further comprising:
a third photoelectric array disposed on the dock body on the first frame and in communication with the power supply, wherein the third photoelectric array is operable to receive the incident light through the cornea, convert the incident light into electrical power, and transmit the electrical power to the power supply for charging the power supply,
wherein the controller is further configured to determine an amount of the incident light being received by the second photoelectric array in response to the RLD being attached to the dock, and
wherein the controller is further configured to provide the one or more control signals to the electromechanical lens array based on the determined amount of the incident light being received by the second photoelectric array.

20. The implant device of claim 19, wherein at least one of the first, second and third photoelectric arrays includes a multi-junction photoelectric array.

21. The implant device of claim 14, wherein at least one of the dock body and the RLD body are foldable.

22. The implant device of claim 14, wherein at least one of the dock body and the RLD body are segmented.

23. An intraocular implant device, the implant device comprising:
a dock shaped for positioning inside a lens chamber of an eye, wherein the dock includes a dock body having an anterior side configured to face a cornea of the eye and a posterior side configured to face a retina of the eye, a first frame disposed on the dock body, a power supply disposed on the dock body within the first frame, and a controller disposed on the dock body within the first frame; and
a removable lens device (RLD) shaped for positioning inside the lens chamber of the eye, wherein the RLD includes an RLD body having an anterior side configured to face the cornea of the eye and a posterior side configured to face the retina of the eye, a second frame disposed on the RLD body, a projector disposed on the RLD body within the second frame, and an electromechanical lens array disposed on the RLD body within the second frame, the electromechanical lens array including one or more lenses configured to receive incident light through the cornea, convert the incident light into a focused image, and transmit the focused image to the retina,
wherein the second frame of the RLD is configured to replaceably attach to the first frame of the dock, such that the RLD is replaceably attached to the dock,
wherein the electromechanical lens array is configured to receive electrical power from the power supply of the dock when the RLD is attached to the dock and one or more control signals from the controller when the RLD is attached to the dock, such that the electromechanical lens array is operable to adjust an axial position of the one or more lenses based on the one or more control signals to increase a clarity of the focused image, and
wherein the projector is configured to receive electrical power from the power supply of the dock when the RLD is attached to the dock and one or more control signals from the controller when the RLD is attached to the dock, such that the projector is operable to emit photons onto the retina in a pattern representative of focused image data based on the one or more control signals.

24. The implant device of claim 23, further comprising:
a first power bus and a first data bus disposed on the dock body on the first frame, the first power bus being in communication with the power supply, and the first data bus being in communication with the controller; and
a second power bus and a second data bus disposed on the RLD body on the second frame, the second power bus and the second data bus being in communication with the electromechanical lens array of the RLD and the projector of the RLD,
wherein when the RLD is attached to the dock, the first power bus is in communication with the second power bus, and the first data bus is in communication with the second data bus.

25. The implant device of claim 24, further comprising:
a receiver or transceiver disposed on the dock body on the first frame, the receiver or transceiver configured to wirelessly receive an input signal from an external transmitter and transmit the input signal to the controller,
wherein the controller is further configured to provide the one or more control signals to the projector based on the input signal.

26. The implant device of claim 25, further comprising:
a first photoelectric array disposed on the dock body on the first frame and in communication with the power supply, and wherein the first photoelectric array is operable to receive the incident light through the cornea, convert the incident light into electrical power, and transmit the electrical power to the power supply for charging the power supply.

27. The implant device of claim 26, further comprising:
a second photoelectric array disposed on the RLD body on the second frame, wherein when the RLD is attached to the dock, the second photoelectric array is in communication with the power supply of the dock via the first and second power busses,
and the second photoelectric array is operable to receive the incident light through the cornea, convert the incident light into electrical power, and transmit the electrical power to the power supply for charging the power supply, and
wherein the controller is configured to selectively activate the first and second photoelectric arrays via the first and second data busses and the first and second power busses, such that the controller activates the first photoelectric array to convert the incident light into electrical power in response to the RLD becoming disengaged from the dock, and the controller activates the second photoelectric array to convert the incident light into electrical power in response to the RLD becoming attached to the dock.

28. The implant device of claim 27, further comprising:
a third photoelectric array disposed on the dock body on the first frame and in communication with the power supply, wherein the third photoelectric array is operable to receive the incident light through the cornea, convert the incident light into electrical power, and transmit the electrical power to the power supply for charging the power supply,
wherein the controller is further configured to determine an amount of the incident light being received by the second photoelectric array in response to the RLD being attached to the dock, and
wherein the controller is further configured to provide the one or more control signals to the electromechanical lens array based on the determined amount of the incident light being received by the second photoelectric array.

29. The implant device of claim 28, further comprising one or more of the following:
    wherein at least one of the dock body and the RLD body are foldable;
    wherein at least one of the dock body and the RLD body are segmented;
    wherein at least one of the first, second and third photoelectric arrays includes a multi-junction photoelectric array;
    wherein one or more lenses of the electromechanical lens array include a variable refractive index lens;
    wherein the electromechanical lens array is configured to operate in a dual mode to correct both near-sightedness and far-sightedness; or
    an antenna.

30. The implant device of claim 23, further comprising a ciliary interface module including at least one sensor configured to detect a signal from a ciliary body of the eye.

* * * * *